(12) United States Patent
Van Der Graaf et al.

(10) Patent No.: US 11,006,626 B2
(45) Date of Patent: May 18, 2021

(54) COMPOUNDS FOR PROTECTION OF CELLS

(71) Applicant: Sulfateq B.V., Groningen (NL)

(72) Inventors: Adrianus Cornelis Van Der Graaf, Groningen (NL); Andre Heeres, Groningen (NL); Johannes Paulus Gerardus Seerden, Groningen (NL)

(73) Assignee: Sulfateq B.V., Amsterdam (NL)

( * ) Notice: Subject to any disclaimer, the term of this patent is extended or adjusted under 35 U.S.C. 154(b) by 0 days.

(21) Appl. No.: 16/143,471

(22) Filed: Sep. 27, 2018

(65) Prior Publication Data

US 2019/0098890 A1 Apr. 4, 2019

Related U.S. Application Data

(62) Division of application No. 14/654,046, filed as application No. PCT/NL2013/050915 on Dec. 18, 2013, now Pat. No. 10,123,529.

(30) Foreign Application Priority Data

Dec. 19, 2012 (NL) ..................................... 2010010

(51) Int. Cl.
| | | |
|---|---|---|
| A61K 31/355 | (2006.01) | |
| A01N 1/02 | (2006.01) | |
| C07D 311/66 | (2006.01) | |
| C07D 311/72 | (2006.01) | |
| C07D 405/06 | (2006.01) | |
| C07D 401/06 | (2006.01) | |
| C07D 311/74 | (2006.01) | |

(52) U.S. Cl.
CPC ......... *A01N 1/0221* (2013.01); *A01N 1/0205* (2013.01); *A01N 1/0226* (2013.01); *C07D 311/66* (2013.01); *C07D 311/72* (2013.01); *C07D 311/74* (2013.01); *C07D 401/06* (2013.01); *C07D 405/06* (2013.01)

(58) Field of Classification Search
CPC ... A01N 1/0221; A01N 1/0226; A61K 31/355
See application file for complete search history.

(56) References Cited

U.S. PATENT DOCUMENTS

| | | | |
|---|---|---|---|
| 5,889,032 A | 3/1999 | Lohray et al. | |
| 6,833,236 B1 | 12/2004 | Stienstra | |
| 7,964,339 B2 | 6/2011 | Scott et al. | |
| 2003/0078420 A1 | 4/2003 | Chabrier de Lassauniere | |
| 2009/0118257 A1 | 5/2009 | Jankowski | |

FOREIGN PATENT DOCUMENTS

| | | |
|---|---|---|
| CA | 2073479 | 1/1994 |
| EP | 0183869 | 12/1984 |
| EP | 1006108 | 12/1999 |
| EP | 1221835 | 4/2003 |
| FR | 2945938 | 12/2010 |
| JP | S 49-088876 A | 8/1974 |
| JP | S 63-264476 A | 11/1988 |
| JP | H 05-058891 A | 3/1993 |

(Continued)

OTHER PUBLICATIONS

NL Search issued on Jun. 17, 2013 for application NL2010010.

(Continued)

*Primary Examiner* — Jeffrey S Lundgren
*Assistant Examiner* — Chris E Simmons
(74) *Attorney, Agent, or Firm* — David P. Owen; Hoyng Rokh Monegier LLP

(57) ABSTRACT

This invention is related to a compound with the structural formula (I)

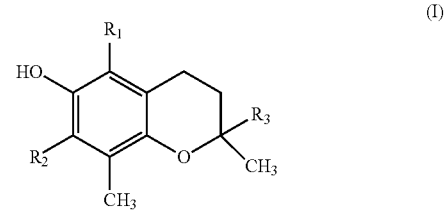

wherein,

R1, and R2 are independently selected from the group consisting of $C_1$-$C_6$ alkyl and is preferably methyl, ethyl, propyl or isopropyl;

R3 is selected from the group consisting of $CH_2NHR_9$, $C(=O)YR_{10}$, —CH2OH

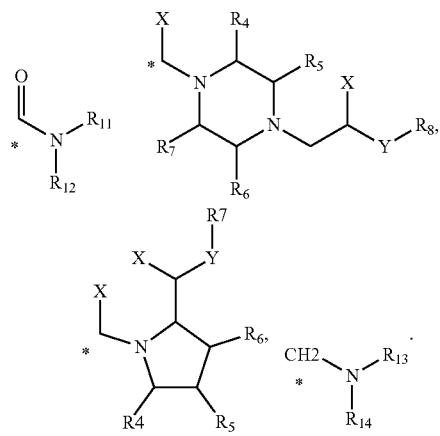

FIG. 1

5 Claims, 4 Drawing Sheets

(56) References Cited

FOREIGN PATENT DOCUMENTS

| | | |
|---|---|---|
| JP | H 06-172339 A | 6/1994 |
| JP | 2001-518068 A | 11/1997 |
| JP | H 10-147575 A | 6/1998 |
| JP | 2003-531200 A | 11/2001 |
| JP | 2002-501018 A | 1/2002 |
| JP | 2002-520317 A | 7/2002 |
| WO | WO88/008424 | 4/1988 |
| WO | WO9741121 | 11/1997 |
| WO | WO2000/000194 | 6/1999 |
| WO | WO03024943 | 3/2003 |
| WO | WO2011128458 | 10/2011 |

OTHER PUBLICATIONS

International Search report dated Mar. 19, 2014 for PCT/NL2013/050915.

European Search report dated Oct. 19, 2018 for application EP18174182.

Jacobsen E Jon et al: "2-(Aminomethyl)chromans that inhibit iron-dependent lipid peroxidation and protect against central nervous system trauma and ischemia", Journal of Medicinal Chemistry, American Chemical Society, US, vol. 35, No. 23, Jan. 1, 1992 (Jan. 1, 1992), pp. 4464-4472.

Koufaki, et al., "Synthesis of Tropolone Derivatives and Evaluation of their In Vitro Neuroprotective Activity", European Journal of Medicinal Chemistry, 2010, vol. 45, pp. 1107-1112.

Koufaki, et al., "Synthesis of a Second Generation Chroman/ Catechol Hybrids and Evaluation of Their Activity in Protecting Neuronal Calls from Oxidative Stress-Induced Cell Death", Bioorganic and Medicinal Chemistry, 2010, vol. 18, pp. 3898-3909.

Koufaki, et al., "Isoxazole Substituted Chromans Against Oxidative Stress-Induced Neuronal Damage", Bioorgaics & Medicinal Chemistry, 2011, vol. 19, pp. 4841-4850.

Koufaki, et al., "Design and Synthesis of Novel Neuroprotective 1,2-Dithiolane/ Chroman Hybrids", Bioorganic & Medicinal Chemistry, 2009, vol. 17, pp. 6432-6441.

Floyd, et al., "Translational Research involving Oxidative Stress and Diseases of Aging", Free Radical & Biology Medicine, 2011, vol. 51, pp. 931-941.

Amorini, et al, "Evaluation of Biochemical Parameters in Platelet Concentrates Stored in Glucose Solution", Blood Transfus, 2007: vol. 5, pp. 24-32.

J. G. Cannon Chapter Nineteen in Burger's Medicinal Chemistry and Drug Discovery, Fifth Edition, vol. I: Principles and Practice, Wiley-Interscience 1995, pp. 783-802, 784.

Figure 2:
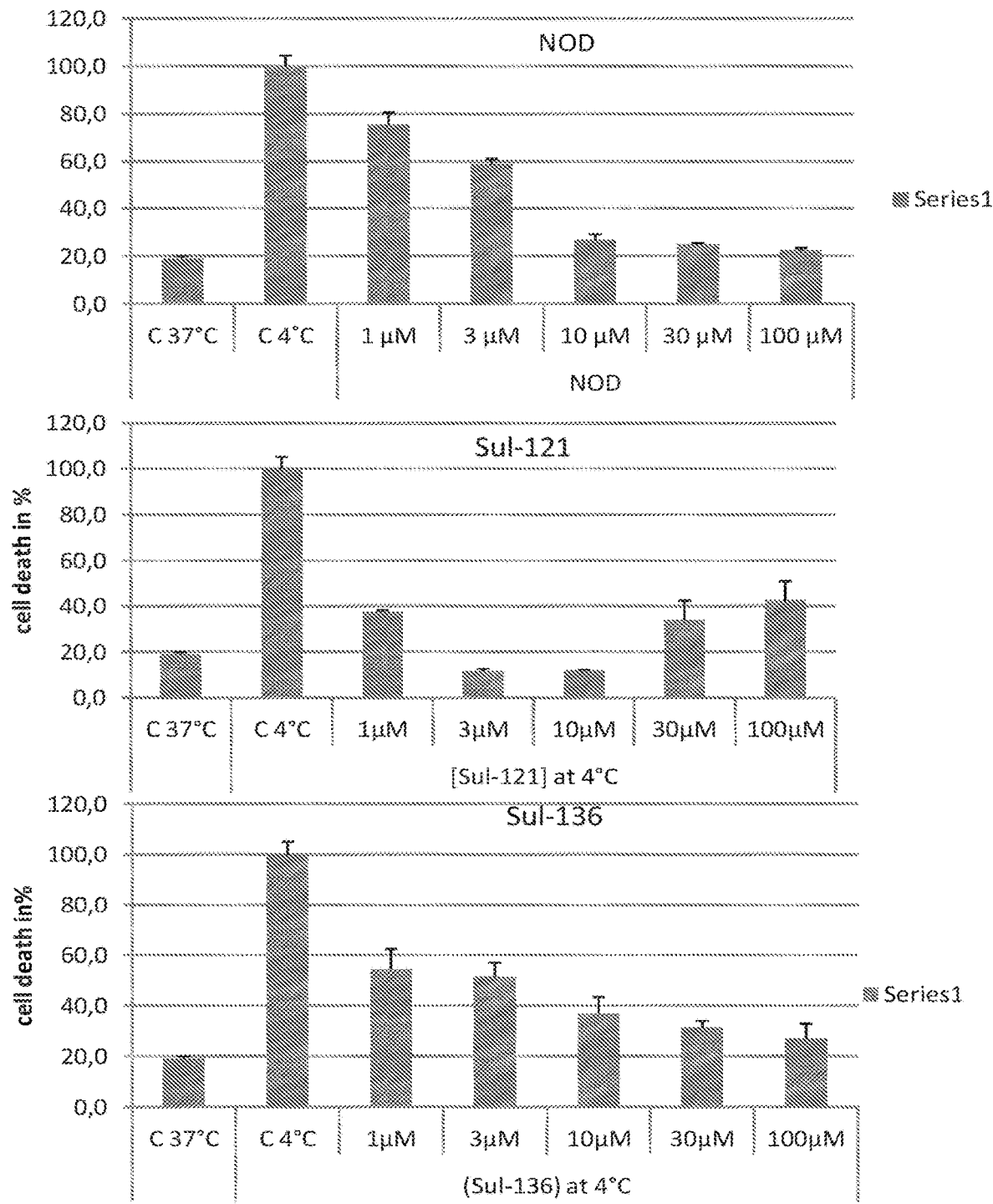
Figure 2:
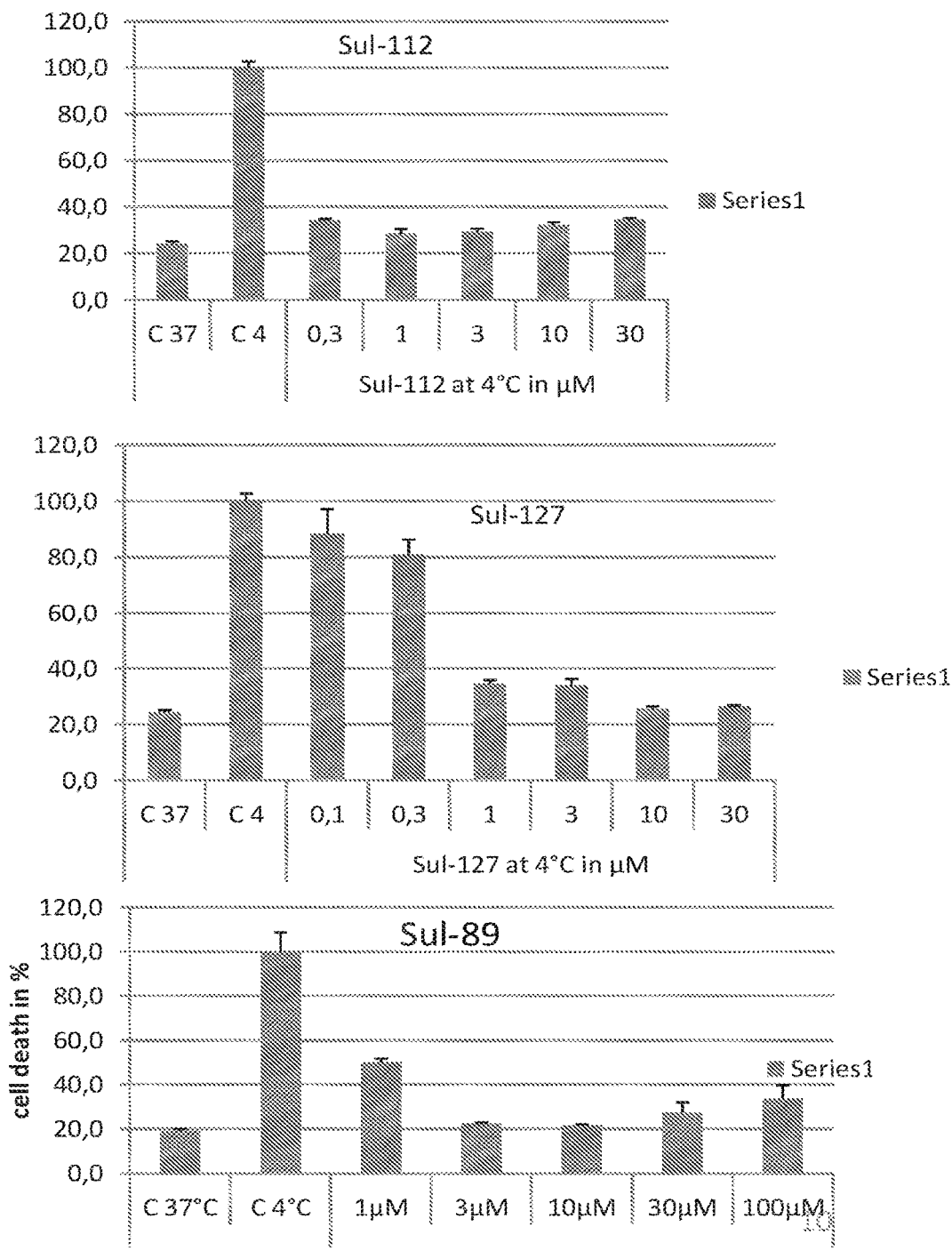

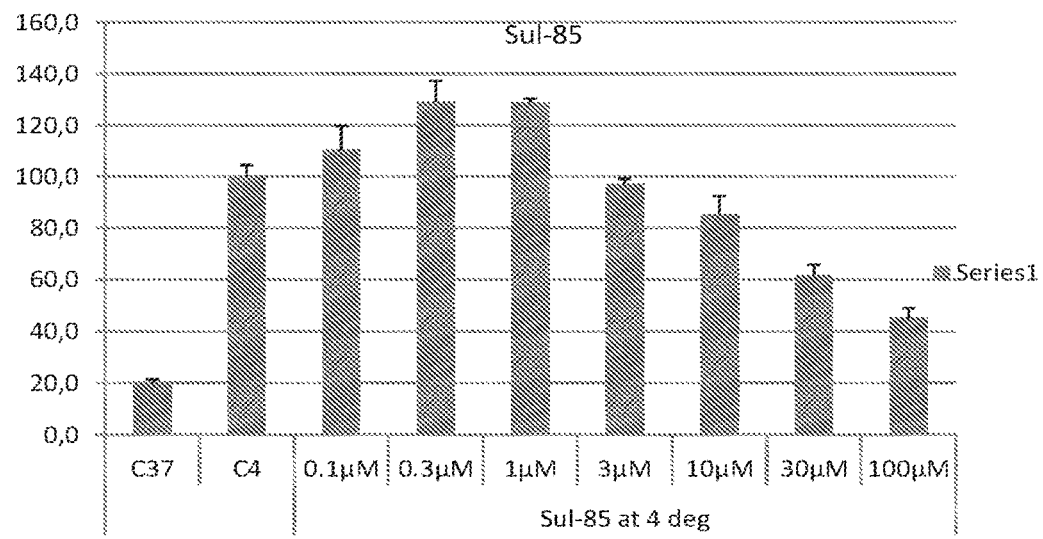
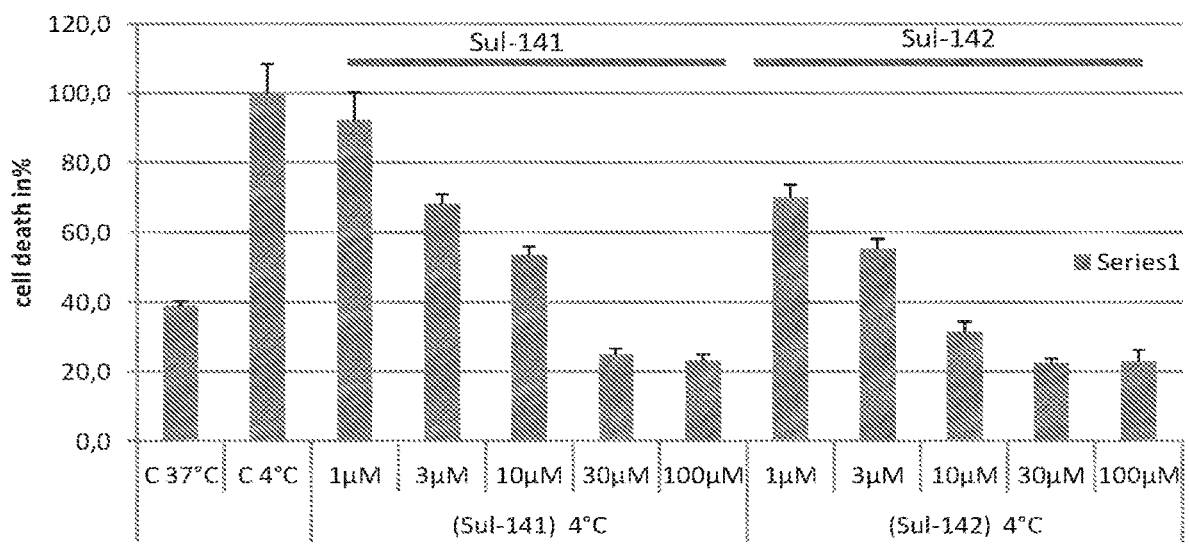
FIG. 2 end

COMPOUNDS FOR PROTECTION OF CELLS

This application is a divisional of U.S. application Ser. No. 14/654,046 filed on 19 Jun. 2015, which is a national stage entry of PCT/NL2013/050915 filed on 18 Dec. 2013, which claims priority from application NL 2010010 filed on 19 Dec. 2012. All these applications are hereby incorporated by reference in their entirety.

BACKGROUND OF THE INVENTION

This invention is related to compounds for the protection of cells, in particular cultured cells, blood and tissue cells and blood platelets, or thrombocytes. It is further related to compounds for use as or in medicaments. In addition it is related to a receptacle comprising the compounds and cells, in particular mammalian cells and mammalian blood platelets, for the protection of the cells. Further, the invention is related to a method for protection of cells, in particular a method for protection of cells during storage.

Compounds that protect cells and that are used as a medicament for protecting cells against, for example oxidative stress-induced cell damage are known in the art. For example tropolone derivatives show neuroprotective activity as described in Koufaki et al. (Eur J Med Chem. 2010 March; 45(3):1107-12). Oxidative stress in cells and cell damage are often related with aging and diseases related to aging. Recent studies revealed that compounds such as nitrones can be used in the treatment of ischemic stroke and as anti-cancer agents (reviewed in Floyd et al. *Free Radic Biol Med.* 2011 Sep. 1; 51 (5):931-41).

Other examples of compounds which present cell protective properties, in particular neuroprotective activity, are hybrids of chroman and catechol moieties as described in Koufaki et al. (Bioorg Med Chem. 2010 Jun. 1; 18(11):3898-909; Bioorg Med Chem. 2009 Sep. 1; 17(17):6432-41), and isoxazole substituted chromans (Bioorg Med Chem. 2011 Aug. 15; 19(16):4841-50).

Cell protection is also required during storage of cells. This is especially the case when cells are cooled down to e.g. 4° C. or −80° C., and warmed again for use in cell assays or clinical applications.

Blood platelets are cell types that are very difficult to store. Currently, blood platelets are stored under constant agitation at 20-24° C. Storage at room temperature provides an environment where any bacteria, skin flora or other blood or skin borne micro-organisms that are introduced to the blood component during the collection process may proliferate, since growth at these temperatures is not limited. These contaminated blood platelets can no longer be used for transfusion. For this reason, storage may not be longer than five days, which results in the fact that more than 15% of the collected blood platelets are expired before they can be used (are/can or were/could). Storage at low temperature would prevent bacterial proliferation. However, platelets show cold induced platelet storage lesion (PSL), [since this abbreviation is used later on] when they are cooled, even briefly to 4° C. These platelet cold storage lesions begin to occur even after brief exposure to temperatures less than 20° C. and are even observed in patients undergoing surgery during which the temperature of the whole body or of parts of the body is decreased to less than 20° C. Platelet exposure to temperatures of less than 20° C. results in structural injury and functional activation of normal platelets. Key characteristics of platelet cold storage lesion are (1) reversible to irreversible morphological change from a discoid cell to speculated spheres with protruding filipodia, depending on the duration of exposure to temperatures less than 20° C. and (2) irreversible immune independent microaggregation of platelets by increased cell-cell interaction, (3) membrane clustering of the glycoprotein GPIb on the surface of platelets, which is the signal for microphages to remove the platelets from the bloodstream; and (4) subsequent recognition and phagocytosis of transfused platelets by macrophages upon transfusion into a recipient. Several compounds and their effect on the storage of platelets have been studied. For example, U.S. Pat. No. 7,964,339 describes the use of polyethylene glycol and derivatives to modify platelets which has an effect on cold storage. Further, Amorini (Blood Transfus. 2007 January; 5(1):24-32) showed that a glucose solution may have a positive effect on the storage of blood platelets. U.S. Pat. No. 6,833,236 and EP patent no. 1 221 835 B1 describe the use of trehalose for protection of thrombocytes when they are freeze-dried or dried in an FTS dryer, for storage of the blood platelets.

Despite this knowledge of compounds which have an effect on the storage of blood platelets, there is a further need to elaborate new compounds which have a positive effect on the storage of blood platelets. In addition, it is further required to find new compounds which protect cells against cell damage in vitro and in vivo, where the cell damage can be caused by oxidative stress, among others.

It is an object of this invention to provide compounds that can be used to protect cells, such as mammalian cells, against cell injury.

It is another object to provide compounds that can be used to protect blood platelets against cold storage lesion.

It is further an object to provide compounds that provide protection of cells against damage caused by several medical indications, such as indications involved by aging diseases, indications involved by oxidative stress, and/or indications involved by the formation of a blood clot.

These objects and other objects are solved partially, if not, completely by a compound as described in the attached claim 1.

In particular, these objects and other objects are solved partially, if not completely, by a compound with the structural formula (I)

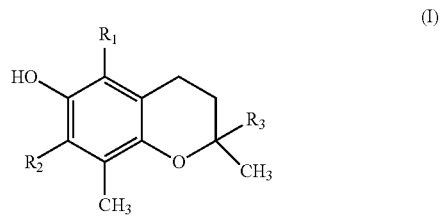

wherein,

R1, and R2 are independently selected from the group consisting of $C_1$-$C_6$ alkyl and is preferably methyl, ethyl, propyl or isopropyl;

R3 is selected from the group consisting of $CH_2NHR_9$, $C(=O)YR_{10}$, —CH2OH,

-continued

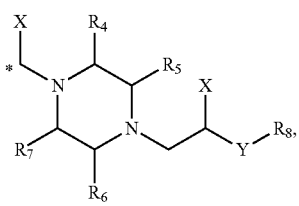
(iii)

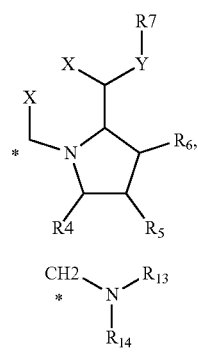
(iv)

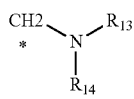
(v)

where * indicates the point of attachment of $R_3$ to the remainder of the molecule;

$R_4$, $R_5$, $R_6$, $R_7$, $R_8$ are independently selected from the group consisting of H, —OH, alkyl, substituted alkyl, preferably hydroxyalkyl, aryl, substituted aryl, halogen, oxygen, heteroaryl, substituted heteroaryl; preferably wherein $R_7$ is not aryl, X is selected from the group consisting of H, =O, =S;

Y is selected from the group consisting of O, NH, S;

$R_9$ is selected from the group consisting of hydrogen, alkyl, substituted alkyl, preferably hydroxyalkyl, alkenyl, aryl, heteroaryl;

$R_{10}$ is selected from the group consisting of alkyl, substituted alkyl, preferably hydroxyalkyl or cyanoalkyl, aryl, OH;

$R_{11}$ and $R_{12}$ together with the atom N to which they are attached form a saturated or unsaturated 3, 4, 5, 6, 7 or 8 membered ring, incorporating one or more additional, such as one, two, or three N, O, or S atoms;

$R_{13}$ and $R_{14}$ together with the atom N to which they are attached form a saturated or unsaturated 3, 4, 5, 6, 7 or 8 membered ring, optionally substituted with alkylalcohol, and in case that $R_3$ is $CH_2NHR_9$, $C(=O)YR_{10}$, —CHOH or

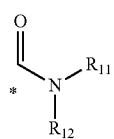

than is $R_1$ and $R_2$ isopropyl.

In one embodiment of the present compounds, $R_7$ or $R_{10}$ is not OH if Y is O.

In one embodiment, the present compound is not 5-[4-[N-[(2RS)-6-hydroxy-2,5,7,8-tetrametylchroman-2-ylmethyl]-(2S)-pyrrolidine-2-methoxy]phenyl methylene]thiazolidine-2,4-dione.

In one embodiment, the invention is related to the present compounds for use as a medicament.

In one aspect, the invention is further related to the use of a compound in treatment or prophylaxis of ischemic stroke, cerebral seizure, thrombosis, embolism, hemorrhage, cardiovascular disease, arthritis, diabetes, cancer, in particular cancer related to aging, atherosclerosis, heart failure, myocardial infarctions, schizophrenia, bipolar disorder, fragile X syndrome, sickle cell disease, and chronic fatigue syndrome, chronic obstructive pulmonary disease (COPD), a neurodegenerative disease such as Alzheimer disease, Parkinson disease, Lou Gehrig's disease, Huntington's disease, hypothermia/reperfusion injury, hemorrhagic shock, aging, hypertension, renal failure due to various kidney diseases, asthma, inflammatory bowel disease, hepatitis and liver cirrhosis, migraine, hyper-homocysteinemia, infection diseases involved in attacking thrombocytes, such as haemorhorragic fever, in particular ebola and chagas wherein the compound has the structural formula of (I)

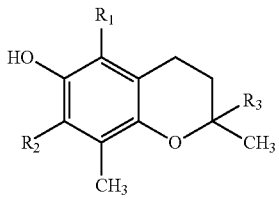
(I)

wherein,

R1, and R2 are independently selected from the group consisting of $C_1$-$C_6$ alkyl and is preferably methyl, ethyl, propyl or isopropyl;

R3 is selected from the group consisting of —CH2OH, $CH_2NHR_9$, $C(=O)$ $YR_{10}$,

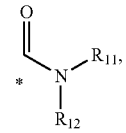
(ii)

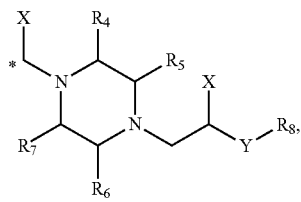
(iii)

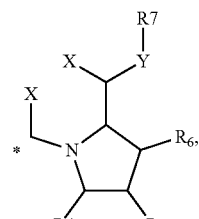
(iv)

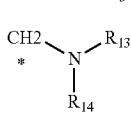
(v)

where * indicates the point of attachment of $R_3$ to the remainder of the molecule;

$R_4$, $R_5$, $R_5$, $R_7$, $R_8$ are independently selected from the group consisting of H, —OH, alkyl, substituted alkyl, preferably hydroxyalkyl, aryl, substituted aryl, halogen, oxygen, heteroaryl, substituted heteroaryl;

X is selected from the group consisting of H, =O, =S;

Y is selected from the group consisting of O, NH, S;

$R_9$ is selected from the group consisting of hydrogen, alkyl, substituted alkyl, preferably hydroxyalkyl or substituted hydroxyalkyl, alkylbenzylfluoride, alkenyl, aryl, substituted aryl, preferably haloaryl, heteroaryl;

$R_{10}$ is selected from the group consisting of hydrogen, alkyl, substituted alkyl, preferably hydroxyalkyl or cyanoalkyl, haloalkyl, alkylamide, substituted alkylamide, aryl, substituted aryl, preferably nitrobenzyl, halobenzyl, alkylbenzoyl, OH, alkenyl, alkadienyl, alkylhalide, arylhalide, —CH$_2$(C=O)O-alkyl, heteroaryl, substituted heteroaryl, —NH—CH$_2$CH$_2$CN;

$R_{11}$ or $R_{12}$, alkyl, substituted alkyl, preferably an alkylamine, or form together with the atom N to which they are attached a saturated or unsaturated 3, 4, 5, 6, 7 or 8 membered ring, optionally incorporating one or more additional, such as one, two, or three N, O, or S atoms, optionally substituted with an alkyl, alkylalcohol;

$R_{13}$ and $R_{14}$ together with the atom N to which they are attached form a saturated or unsaturated 3, 4, 5, 6, 7 or 8 membered ring, optionally incorporating one or more additional, such as one, two, or three N, O, or S atoms, optionally substituted, preferably substituted with an alkyl, alkylalcohol;

The compounds of general formula (I) containing an assymetrical centre are of isomeric form. The racemic and enantiomeric forms of these compounds also form part of this invention.

The inventors surprisingly found that the compounds having the formula as described above protect cells against cell damage. The inventors developed several new compounds as described above, and found that they are able to protect cells against cell damage. Cell damage can have several causes and is established under stress conditions. Cell damage may eventually lead to cell necrosis or apoptosis. The inventors performed tests on several cell types and surprisingly found that the above compounds have an effect on the cells and protect the cell against cell damage or cell injury under stress conditions. With stress conditions is understood oxygen deprivation (hypoxia and ischemia); occurrence of physical agents (such as mechanical trauma, extremes of temperature, burns and deep cold, sudden changes in atmospheric pressure, radiations, electric shock); occurrence of chemical agents and drugs; occurrence of infectious agents, immunologic reactions; genetic diseases; nutritional imbalances, such as injury, infection, cancer, infarction, poisons, occurrence of ROS (Reactive Oxygen Species), and inflammation. Compounds according to the invention can be used as a medicament to protect cells against the above mentioned causes of cell injury.

In one embodiment, the invention is related to the compounds as described above for use in treatment of oxidative stress, inflammation, derailment of proteostasis, DNA damage (e.g. irradiation), calcium overload, poisons/toxic agents, derailment or errors of metabolism induced cellular damage.

In another embodiment, the invention is related to the compounds as described above for use in treatment or prophylaxis of diseases that are related to aging, neurodegenerative diseases, infection, diabetes and other indication in which cell damage is involved.

In another embodiment, the invention is related to the compounds as described above for the treatment or prophylaxis of conditions related to aging or oxidative stress, in particular ischemic stroke, cerebral seizure, thrombosis, embolism, hemorrhage, cardiovascular disease, arthritis, diabetes, cancer, in particular cancer related to aging, atherosclerosis, heart failure, myocardial infarctions, schizophrenia, bipolar disorder, fragile X syndrome, sickle cell disease, chronic fatigue syndrome, chronic obstructive pulmonary disease (COPD) and neurodegenerative diseases such as Alzheimer disease, Parkinson disease, Lou Gehrig's disease and Huntington's disease, tissue damage mediated by a viral or bacterial infection.

In another embodiment, the invention is related to a compound as described above for use in treatment of ischemia/reperfusion injury.

In another embodiment, the invention is related to a compound as describe above for use in treatment of indications involved with oxidative stress induced cell damage.

In one aspect, the inventors also found that the compounds as described above protect blood platelets and prevent blood platelets to adhere or aggregate, and prevent to undergo the shape-change.

In another embodiment, the invention is related to a compound for use in the treatment or prophylaxis of disorders leading to or caused by a platelet disfunction such as arterial thrombosis, arterial fibrillation, pulmonary embolism (PE), deep vein thrombosis (DVT), or venous thromboembolism (VTE), congestive heart failure, stroke, myocardial infarction, genetic or acquired hypercoagulability, or platelet defects caused by haemorhorrgic fevers such as ebola, Marburg disease and chagas.

In a preferred embodiment, the compound for use in the treatment or prophylaxis of disorders leading to or caused by a platelet disfunction is chosen from Sul 100, Sul 117, Sul 118, Sul 120, Sul 121, Sul 125, Sul 126, Sul 132, Sul 136, Sul 138, Sul 139, Sul 141, Sul 142, Sul 143, Sul 144, Sul 145 (see table 1 for IUPAC names).

In another aspect, the invention is related to a solution comprising the compounds as described above and cells. The inventors found that the compounds protect the cells against cell injury, which may eventually lead to cell death via necrosis or apoptosis. The compounds according to the invention provide protection against cell injury. The protection can be provided during storage. Cells stored with compounds according to the invention have a decreased cell death compared with cells stored without the compound.

In one embodiment, the above compounds protect mammalian cells, such as cultured cell lines (e.g. from human origin), stem cells, primary cells, blood platelets, blood cells and tissue cells. The cell lines can be brought in culture for the manufacture of viral vaccines, biological products produced by recombinant DNA technology in the cell cultures, such as proteins, hormones, enzymes, antibodies, etc.

In another embodiment, the invention is related to a medium comprising one of the above compounds, in which cells which are grown to form a two- or three dimensional cell culture. In addition, the compounds can be used to protect cells that are used for tissue engineering.

Preferred compounds according to this embodiment are compounds selected from the group consisting of those listed in Table 1.

TABLE 1

| Code | Chemical name |
| --- | --- |
| SUL-083 | 2,2,5,7,8-pentamethylchroman-6-ol |
| SUL-084 | (S)-6-hydroxy-2,5,7,8-tetramethylchroman-2-carboxylic acid |
| SUL-085 | (R)-6-hydroxy-2,5,7,8-tetramethylchroman-2-carboxylic acid |
| SUL-089 | 6-hydroxy-2,5,7,8-tetramethylchroman-2-carboxamide |
| SUL-090 | N,6-dihydroxy-2,5,7,8-tetramethylchroman-2-carboxamide; |
| SUL-091 | N-butyl-6-hydroxy-2,5,7,8-tetramethylchroman-2-carboxamide; |
| SUL-092 | 6-hydroxy-N-isopropyl-2,5,7,8-tetramethylchroman-2-carboxamide; |
| SUL-093 | (E)-N-(3,7-dimethylocta-2,6-dien-1-yl)-6-hydroxy-2,5,7,8-tetramethylchroman-2-carboxamide; |
| SUL-095 | (6-hydroxy-2,5,7,8-tetramethylchroman-2-yl)(morpholino)methanone; |
| SUL-097 | N-(4-fluorobenzyl)-6-hydroxy-2,5,7,8-tetramethylchroman-2-carboxamide; |
| SUL-098 | 6-hydroxy-N-((S)-2-hydroxy-1-phenylethyl)-2,5,7,8-tetramethylchroman-2-carboxamide; |
| SUL-100 | 6-hydroxy-2,5,7,8-tetramethyl-N-(2-(methylamino)ethyl)chroman-2-carboxamide; |
| SUL-101 | 6-hydroxy-N,2,5,7,8-pentamethyl-N-(2-(methylamino)ethyl)chroman-2-carboxamide; |
| SUL-102 | 6-hydroxy-2,5,7,8-tetramethyl-N-(3-(piperidin-1-yl)propyl)chroman-2-carboxamide; |
| SUL-104 | 6-hydroxy-2,5,7,8-tetramethyl-N-(3-nitrophenyl)chroman-2-carboxamide; |
| SUL-106 | N-(4-fluorophenyl)-6-hydroxy-2,5,7,8-tetramethylchroman-2-carboxamide; |
| SUL-107 | methyl 4-(6-hydroxy-2,5,7,8-tetramethylchroman-2-carboxamido)benzoate; |
| SUL-108 | (4-butylpiperazin-1-yl)(6-hydroxy-2,5,7,8-tetramethylchroman-2-yl)methanone; |
| SUL-109 | (6-hydroxy-2,5,7,8-tetramethylchroman-2-yl)(4-(2-hydroxyethyl)piperazin-1-yl)methanone; |
| SUL-110 | ((2S,5R)-4-allyl-2,5-dimethylpiperazin-1-yl)(6-hydroxy-2,5,7,8-tetramethylchroman-2-yl)methanone; |
| SUL-111 | N-((R)-2-amino-2-oxo-1-phenylethyl)-6-hydroxy-2,5,7,8-tetramethylchroman-2-carboxamide; |
| SUL-112 | (6-hydroxy-2,5,7,8-tetramethylchroman-2-yl)((S)-2-(hydroxymethyl)pyrrolidin-1-yl)methanone; |
| SUL-114 | N-(2-bromoethyl)-6-hydroxy-2,5,7,8-tetramethylchroman-2-carboxamide; |
| SUL-115 | N'-(2-cyanoethyl)-6-hydroxy-2,5,7,8-tetramethylchroman-2-carbohydrazide; |
| SUL-116 | 2-(((4-fluorobenzyl)amino)methyl)-2,5,7,8-tetramethylchroman-6-ol; |
| SUL-117 | 2-((butylamino)methyl)-2,5,7,8-tetramethylchroman-6-ol; |
| SUL-118 | 6-hydroxy-5,7-diisopropyl-2,8-dimethylchroman-2-carboxylic acid; |
| SUL-119 | 2-(hydroxymethyl)-5,7-diisopropyl-2,8-dimethylchroman-6-ol; |
| SUL-120 | 6-hydroxy-N-((R)-1-hydroxypropan-2-yl)-2,5,7,8-tetramethylchroman-2-carboxamide |
| SUL-121 | (6-hydroxy-2,5,7,8-tetramethylchroman-2-yl)(piperazin-1-yl)methanone |
| SUL-122 | (6-hydroxy-2,5,7,8-tetramethylchroman-2-yl)(4-(2-(2-hydroxyethoxy)ethyl)piperazin-1-yl)methanone; |
| SUL-123 | N-(2-cyanoethyl)-6-hydroxy-2,5,7,8-tetramethylchroman-2-carboxamide; |
| SUL-124 | 6-hydroxy-N-(2-((2-hydroxyethyl)(methyl)amino)ethyl)-2,5,7,8-tetramethylchroman-2-carboxamide; |
| SUL-125 | (R)-N,6-dihydroxy-2,5,7,8-tetramethylchroman-2-carboxamide; |
| SUL-126 | (S)-N,6-dihydroxy-2,5,7,8-tetramethylchroman-2-carboxamide; |
| SUL-128 | 2-(((S)-2-(hydroxymethyl)pyrrolidin-1-yl)methyl)-2,5,7,8-tetramethylchroman-6-ol; |
| SUL-129 | 2-((((S)-2-hydroxy-1-phenylethyl)amino)methyl)-2,5,7,8-tetramethylchroman-6-ol; |
| SUL-130 | 2,5,7,8-tetramethyl-2-(piperidin-1-ylmethyl)chroman-6-ol; |
| SUL-131 | N,6-dihydroxy-5,7-diisopropyl-2,8-dimethylchroman-2-carboxamide; |
| SUL-132 | (6-hydroxy-2,5,7,8-tetramethylchroman-2-yl)(4-(2-hydroxyethyl)piperazin-1-yl)methanone; |
| SUL-133 | (6-hydroxy-5,7-diisopropyl-2,8-dimethylchroman-2-yl)(4-(2-hydroxyethyl)piperazin-1-yl)methanone; |
| SUL-134 | 2-(((S)-2-(hydroxymethyl)pyrrolidin-1-yl)methyl)-2,5,7,8-tetramethylchroman-6-ol; |
| SUL-135 | 2-(((S)-2-(hydroxymethyl)pyrrolidin-1-yl)methyl)-2,5,7,8-tetramethylchroman-6-ol; |
| SUL-136 | 2-(4-(6-hydroxy-2,5,7,8-tetramethylchroman-2-carbonyl)piperazin-1-yl)acetic acid; |
| SUL-137 | (6-hydroxy-5,7-diisopropyl-2,8-dimethylchroman-2-yl)(piperazin-1-yl)methanone; |
| SUL 138 | (6-hydroxy-2,5,7,8-tetramethylchroman-2-yl)(4-(2-hydroxyethyl)piperazin-1-yl)methanone; |
| SUL-139 | 2-(4-(6-hydroxy-5,7-diisopropyl-2,8-dimethylchroman-2-carbonyl)piperazin-1-yl)acetic acid; |
| SUL-140 | ethyl 2-(4-(6-hydroxy-2,5,7,8-tetramethylchroman-2-carbonyl)piperazin-1-yl)acetate; |
| SUL-141 | (S)-2-(4-(6-hydroxy-2,5,7,8-tetramethylchroman-2-carbonyl)piperazin-1-yl)acetic acid; |
| SUL-142 | (R)-2-(4-(6-hydroxy-2,5,7,8-tetramethylchroman-2-carbonyl)piperazin-1-yl)acetic acid; |
| SUL-143 | (2S)-1-(6-hydroxy-2,5,7,8-tetramethylchroman-2-carbonyl)pyrrolidine-2-carboxylic acid; |

TABLE 1-continued

| Code | Chemical name |
| --- | --- |
| SUL-144 | (2S)-1-(6-hydroxy-2,5,7,8-tetramethylchroman-2-carbonyl)pyrrolidine-2-carboxylic acid; |
| SUL-145 | (2S)-1-(6-hydroxy-2,5,7,8-tetramethylchroman-2-carbonyl)pyrrolidine-2-carboxylic acid; |

A preferred embodiment according to the invention is a medium comprising blood platelets and one of the above compounds.

In a preferred embodiment, blood platelets are protected against and are prevented to adhere or aggregate, or to undergo shape change by the addition of Sul 100, 117, 118, 120, 121, 125, 126, 132, 136, 138, 139, 141, 142, 143, 144, 145.

In another aspect, the invention is related to a method for protection of cells comprising adding a compound as described above to a cell. Preferably, the present method is an ex vivo method. Accordingly, the compound can be used for protection during storage of cells. The storage can occur at a temperature which is suitable for storage of the particular cell and can be at and below 37° C., preferably between −80 and 37° C., such as between 10-25° C.; 0-10° C., about 4° C.; between −20 and 0° C. and between −80 and −20° C., at room temperature, −80° C. etc. The inventors found that the above compounds protect the cells against cell injury during and after cooling down, and especially against injury that occurs during warming up back to the functional temperature. More cells survive these stress conditions and thus the storability increases when the cells are stored together with the compound according to the invention, compared with cells that are stored without the addition of a compound according to the invention.

In one embodiment the medium, which can be a typical platelet storage buffer or additive solution, comprises a compound according to the invention having a concentration that is between $1.10^{-3}$-$1.10^{-30}$M, preferably about $1.10^{-6}$, $1.10^{-7}$, $1.10^{-8}$, $1.10^{-9}$, $1.10^{-10}$M.

In another aspect, the invention is related to a method for storage of cells, wherein the cells are blood platelets comprising adding a compound according to the invention to the blood platelets. As described above, blood platelets are stored at room temperature, before they can be used for transfusion. Storage of blood platelets at 4° C. results in rapid loss of platelet viability and function. The inventors found that when blood platelets are stored at a temperature below 20° C., e.g. at 4° C. with a compound according to the invention, the storability is much higher and can therefore longer be stored compared with blood platelets stored without the compounds. The compound according to the invention can thus be used to obtain an increased storability of blood platelets during cold storage. Moreover, when a compound is added to the blood platelets, the aggregation and adhesion of the blood platelets decrease. Moreover, platelets stored with a compound according to the invention may still show an aggregation response upon stimulation with ADP or epinephrine. The compounds according to the invention help to maintain the functionality of the platelets. The invention is further related to a method for protection of blood platelets against platelet storage lesions. This means that a compound according to the invention is involved in the process which affects morphological changes of platelets when they are cold stored. The compound according to the invention provides a reduced shape change, a decrease in coagulation and has an effect on the release of granule contents, exocytosis of cytosolic proteins or on the glycoprotein patterns on the platelets. The compounds according to the invention have an influence on the platelet activation mechanism, and provide a decrease in PSL (platelet PSL=platelet storage lesion), or decreased amount of activated platelets, subsequently leading to a decrease of apoptosis. The above compounds preserve the platelet function of blood platelets after having been stored in a cold environment.

In this aspect, preferred compounds are Sul 100, Sul 117, Sul 118, Sul 120, Sul 121, Sul 125, Sul 126, Sul 132, Sul 136, Sul 138, Sul 139, Sul 141, Sul 142, Sul 143, Sul 144, Sul 145.

The compounds according to the invention better preserve the capacity of platelets to aggregate or to adhere upon stimulation, even when they have been stored at 4° C.

In one embodiment, the invention provides platelets stored with a compound according to the invention for use as platelet transfusion.

In one embodiment the blood platelets are derived from platelet-rich plasma (PRP). In another embodiment, the platelets are derived from a buffy coat (BC) or the apheresis method. Platelets for transfusion can be prepared by three different methods: (a) the platelet-rich plasma (PRP) method; (b) the buffy coat (BC) method; and (c) the apheresis method. Studies comparing PRP and BC platelets have shown no difference in the in vitro quality of such platelet concentrates when they are stored for up to 5 days at room temperature. In apheresis of platelets or plateletpheresis the platelets are derived from one specific donor. The three methods are well described and are known by the person skilled in the art.

In one embodiment, the present invention relates to the use of the present compounds, preferably Sul 109, for increasing the cold ischemic tolerance of transplant organs, preferably hearts. In other words, the present invention relates also to the use of the present compounds, preferably Sul 109, for storing transplant organs, such as hearts.

The technical effects and advantages of the various embodiments and aspects of the methods of the invention correspond mutatis mutandis to those described for the products of the invention and vice versa.

This then generally describes the invention but to assist with understanding, reference will now be made to the accompanying comparison and non-limiting examples and figures which show embodiments of the invention.

FIGURE DESCRIPTION

Figure 1:
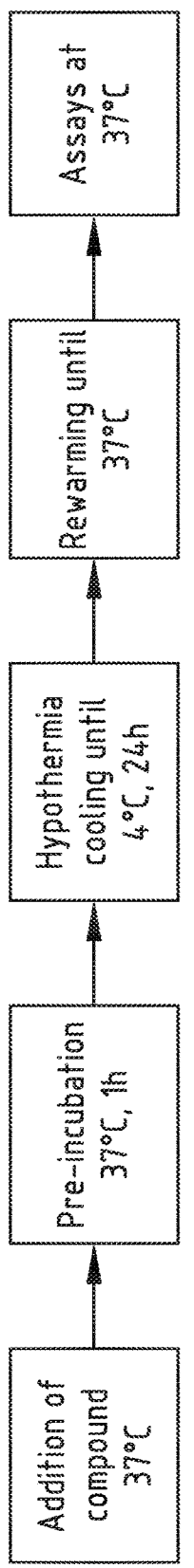

FIG. 1: Schematic overview of hypothermia/reperfusion injury inducing test where the compound of the invention is first added to the cells at 37° C., incubated for 1 h, cooled at 4° C. during 24 h, rewarmed and tested at 37° C.

FIG. 2: Trypan Blue absorption assay. NOD is used as a positive control. Sul 112 ((6-hydroxy-2,5,7,8-tetramethyl-chroman-2-yl) ((S)-2-(hydroxymethyl)pyrrolidin-1-yl) methanone), Sul 121 ((6-hydroxy-2,5,7,8-tetramethylchroman-2-yl) (piperazin-1-yl)methanone) Sul 127 (methyl 6-hydroxy-2,5,7,8-tetramethylchroman-2-carboxylate), Sul 136 (2-(4-(6-hydroxy-2,5,7,8-tetramethylchroman-2-carbonyl)piperazin-1-yl)acetic acid), Sul 89 (6-hydroxy-2,5,7,8-tetramethylchroman-2-carboxamide), Sul 85 (((R)-6-hydroxy-2,5,7,8-tetramethylchroman-2-carboxylic acid), Sul 141 ((S)-2-(4-(6-hydroxy-2,5,7,8-tetramethylchroman-2-carbonyl)piperazin-1-yl)acetic acid), Sul 142 ((R)-2-(4-(6-hydroxy-2,5,7,8-tetramethylchroman-2-carbonyl)piperazin-1-yl)acetic acid). Sul 136 is a racemic mixture. Sul 141 and Sul 142 are respectively the S and R isomer. The compounds were added to SMAC cells at different concentrations. The absorption assay was performed after rewarming until 37° C. 4° C. means that the cells were first cooled until 4° C. C37° C. and C4° C. are tests of SMAC cells wherein the cells are maintained at 37° C. and first cooled at 4° C. and than rewarmed until 37° C., respectively without the presence of compounds.

EXAMPLE 1: PRESERVATION OF HEK CELLS

Material and Method:

Human Embryo Kidney (HEK) 293 cells were cultured in DMEM cell culture medium (Life Technologies, 41965-052) supplemented with fetal calf serum, penicillin and streptomycin. Cells were seeded at a density of 0.8-1.2E6 mL-1 in 25 cm2 polystyrene flasks, placed in a 37° C. C02-regulated humidified incubator and were allowed to proliferate for 24 hours before commencing experiments.

The compounds SUL-090 (N,6-dihydroxy-2,5,7,8-tetramethylchroman-2-carboxamide), SUL-091 (N-butyl-6-hydroxy-2,5,7,8-tetramethylchroman-2-carboxamide), SUL-092 (6-hydroxy-N-isopropyl-2,5,7,8-tetramethylchroman-2-carboxamide), SUL-093 ((E)-N-(3,7-dimethylocta-2,6-dien-1-yl)-6-hydroxy-2,5,7,8-tetramethylchroman-2-carboxamide), SUL-095 ((6-hydroxy-2,5,7,8-tetramethylchroman-2-yl) (morpholino)methanone), SUL-097 (N-(4-fluorobenzyl)-6-hydroxy-2,5,7,8-tetramethylchroman-2-carboxamide), SUL-098 (6-hydroxy-N—((S)-2-hydroxy-1-phenylethyl)-2,5,7,8-tetramethylchroman-2-carboxamide), SUL-100 (6-hydroxy-2,5,7,8-tetramethyl-N-(2-(methylamino)ethyl)chroman-2-carboxamide), SUL-101 (6-hydroxy-N,2,5,7,8-pentamethyl-N-(2-(methylamino)ethyl)chroman-2-carboxamide), SUL-102 (6-hydroxy-2,5,7,8-tetramethyl-N-(3-(piperidin-1-yl)propyl) chroman-2-carboxanide), SUL-104 (6-hydroxy-2,5,7,8-tetramethyl-N-(3-nitrophenyl) chroman-2-carboxamide), SUL-106 (N-(4-fluorophenyl)-6-hydroxy-2,5,7,8-tetramethylchroman-2-carboxamide), SUL-107 (methyl 4-(6-hydroxy-2,5,7,8-tetramethylchroman-2-carboxamido)benzoate), SUL-108 ((4-butylpiperazin-1-yl) (6-hydroxy-2,5,7,8-tetramethylchroman-2-yl)methanone), SUL-109 ((6-hydroxy-2,5,7,8-tetramethylchroman-2-yl) (4-(2-hydroxyethyl)piperazin-1-yl)methanone), SUL-111 (N—((R)-2-amino-2-oxo-1-phenylethyl)-6-hydroxy-2,5,7,8-tetramethylchroman-2-oarboxamide), SUL-112 ((6-hydroxy-2,5,7,8-tetramethylchroman-2-yl) ((S)-2-(hydroxymethyl)pyrrolidin-1-yl)methanone), SUL-114 (N-(2-bromoethyl)-6-hydroxy-2,5,7,8-tetramethylchroman-2-carboxamide), SUL-117 (2-((butylamino)methyl)-2,5,7,8-tetramethylchroman-6-ol), SUL-118 (6-hydroxy-5,7-diisopropyl-2,8-dimethylchroman-2-carboxylic acid), SUL-120 (6-hydroxy-N—((R)-1-hydroxypropan-2-yl)-2,5,7,8-tetramethylchroman-2-carboxamide), SUL-121 ((6-hydroxy-2,5,7,8-tetramethylchroman-2-yl) (piperazin-1-yl)methanone), SUL-122 ((6-hydroxy-2,5,7,8-tetramethylchroman-2-yl) (4-(2-(2-hydroxyethoxy)ethyl) piperazin-1-yl)menthanone), SUL-123 (N-(2-cyanoethyl)-6-hydroxy-2,5,7,8-tetramethylchroman-2-carboxamide), SUL-124 (6-hydroxy-N-(2-((2-hydroxyethyl)(methyl)amino)ethyl)-2,5,7,8-tetramethylchroman-2-carboxamide), SUL-125 ((R)—N,6-dihydroxy-2,5,7,8-tetramethylchroman-2-carboxamide), SUL-126 ((S)—N,6-dihydroxy-2,5,7,8-tetramethylchroman-2-carboxamide, SUL-128 (2-(((S)-2-(hydroxymethyl)pyrrolidin-1-yl)methyl)-2,5,7,8-tetramethylchroman-6-ol), SUL-129 (2-((((S)-2-hydroxy-1-phenylethyl)amino)methyl)-2,5,7,8-tetramethylchroman-6-ol), SUL-130 (2,5,7,8-tetramethyl-2-(piperidin-1-ylmethyl)chroman-6-ol), SUL-131 (N,6-dihydroxy-5,7-diisopropyl-2,8-dimethylchroman-2-carboxamide), SUL-132 ((6-hydroxy-2,5,7,8-tetramethylchroman-2-yl) (4-(2-hydroxyethyl)piperazin-1-yl)methanone), SUL-134 (2-(((S)-2-(hydroxymethyl)pyrrolidin-1-yl)methyl)-2,5,7,8-tetramethylchroman-6-ol), SUL-135 (2-(((S)-2-(hydroxymethyl)pyrrolidin-1-yl)methyl)-2,5,7,8-tetramethylchroman-6-ol), SUL-136 (2-(4-(6-hydroxy-2,5,7,8-tetramethylchroman-2-carbonyl)piperazin-1-yl)acetic acid), SUL-137 ((6-hydroxy-5,7-diisopropyl-2,8-dimethylchroman-2-yl) (piperazin-1-yl)methanone), SUL 138 ((6-hydroxy-2,5,7,8-tetramethylchroman-2-yl)(4-(2-hydroxyethyl)piperazin-1-yl)methanone), SUL-139 (2-(4-(6-hydroxy-5,7-diisopropyl-2,8-dimethylchroman-2-carbonyl) piperazin-1-yl)acetic acid), SUL-140 (ethyl 2-(4-(6-hydroxy-2,5,7,8-tetramethylchroman-2-carbonyl)piperazin-1-yl)acetate), SUL-141 ((S)-2-(4-(6-hydroxy-2,5,7,8-tetramethylchroman-2-carbonyl)piperazin-1-yl)acetic acid), SUL-142 ((R)-2-(4-(6-hydroxy-2,5,7,8-tetramethylchroman-2-carbonyl)piperazin-1-yl)acetic acid), SUL-143 ((2S)-1-(6-hydroxy-2,5,7,8-tetramethylchroman-2-carbonyl)pyrrolidine-2-carboxylic acid), SUL-144 ((2S)-1-(6-hydroxy-2,5,7,8-tetramethylchroman-2-carbonyl)pyrrolidine-2-carboxylic acid), SUL-145 ((2S)-1-(6-hydroxy-2,5,7,8-tetramethylchroman-2-carbonyl)pyrrolidine-2-carboxylic acid were tested.

The compounds were dissolved in dimethyl sulfoxide (DMSO) to several concentrations. Before commencing experiments, this stock solution was dissolved in pre-warmed DMEM and further diluted to obtain a concentration range from 10 nM-1 mM. The hypothermia rewarming injury protocol was used as follows and is summarized in FIG. 1. Cell culture medium was then replaced by these dilutions and cells were incubated in the presence of the compound for 1 hour. After incubation, lids were closed tightly and flasks were placed in a 4° C. room and cooled for 24 hours. After this cooling period, cells were placed back in the 37° C. incubator with lids closed and were allowed to rewarm for another 24 hours.

Assessment of Viability

After this rewarming period, microscopic images were taken to assess cell morphology (Nikon D5100, Nikon Diaphot-TMD). Cell culture medium was collected and centrifuged (4 minutes, 2000 rpm). The supernatant was collected and pH was immediately measured to prevent equilibration of the pH by the carbonate buffer in the medium, while the pelleted cells were resuspended in 5 mL of PBS. Cells remaining in the flask were washed twice with phosphate buffered saline (PBS) while the washing product was discarded. Subsequently, the cells were trypsinized by addition of 0.5 mL of trypsine and pooled with the resuspended pellet. This cell suspension was then stained at a final concentration of 0.2% trypan blue (Sigma, T8154), followed by manual assessment of viability and cell number on a Bürker-Türk hemocytometer. To conclude the assay, cell culture medium glucose levels were measured (Roche Accutrend Plus) as an indication of metabolic activity. All of these steps were performed with care to prevent mechanical stress to influence or alter the viability of the cells after cooling.

Results

Table 2 shows the results of the amount of cells that survived the process of cooling and rewarming with the addition of the compound according to the invention in different concentration. The amount represents the % cells that survived. The number of the compound corresponds with the compound as described in table 1. In the control, the same procedure was applied to two badges of HEK cells. The medium did not comprise a compound according to the invention. The amount of cells that survived depends on the used concentration and on the type of compound.

TABLE 2

|  | 10 nM | 100 nM | 1 µM | 10 µM | 100 µM | 1 mM | Mean |
|---|---|---|---|---|---|---|---|
| SUL - 17 |  | 91.95 | 93.10 | 91.77 | 95.58 | 95.34 | 94 |
| SUL - 83 |  | 0.00 | 79.38 | 70.12 | 55.74 | 1.11 | 41 |
| SUL - 84 |  | 6.22 | 19.79 | 70.08 | 95.74 | 94.50 | 57 |
| SUL - 85 |  | 1.23 | 0.00 | 1.43 | 84.88 | 78.26 | 33 |
| SUL - 89 |  | 34.90 | 88.63 | 91.61 | 87.57 |  | 76 |
| SUL - 90 |  | 8.67 | 91.34 | 90.25 | 77.92 | 20.41 | 58 |
| SUL - 91 |  | 2.28 | 82.44 | 89.53 | 87.54 | 0.00 | 52 |
| SUL - 92 |  | 3.13 | 64.58 | 87.14 | 86.47 | 1.55 | 49 |
| SUL - 93 |  | 97.05 | 96.08 | 84.04 | 21.69 | 8.00 | 61 |
| SUL - 94 |  | 98.63 | 97.31 | 96.35 | 89.02 | 0.00 | 76 |
| SUL - 95 |  | 2.76 | 86.75 | 90.38 | 92.09 | 85.86 | 72 |
| SUL - 96 |  | 5.62 | 96.34 | 93.53 | 96.88 | 0.00 | 58 |
| SUL - 97 |  | 0.00 | 95.11 | 96.37 | 91.62 | 5.17 | 58 |
| SUL - 98 |  | 90.99 | 97.81 | 97.54 | 88.49 | 1.02 | 75 |
| SUL - 99 | 54.44 |  | 87.98 | 93.75 | 69.18 | 100.00 | 81 |
| SUL - 100 | 77.78 | 76.87 | 63.25 | 68.77 | 55.61 | 0.00 | 57 |
| SUL - 102 | 73.24 | 95.77 | 93.72 | 81.97 | 73.41 | 93.33 | 85 |
| SUL - 103 | 99.74 | 98.10 | 96.85 | 98.31 | 10.27 | 0.00 | 67 |
| SUL - 104 | 99.26 | 99.49 | 97.52 | 98.91 | 40.91 | 52.17 | 81 |
| SUL - 105 | 94.72 | 95.01 | 80.50 | 96.11 | 32.86 | 50.64 | 75 |
| SUL - 106 | 77.78 | 76.87 | 63.25 | 68.77 | 55.61 | 0.00 | 57 |
| SUL - 107 | 4.42 | 95.74 | 92.72 | 94.77 | 37.62 | 28.92 | 59 |
| SUL - 108 | 0.00 | 40.89 | 94.15 | 96.81 | 96.57 | 0.00 | 55 |
| SUL - 109 | 92.64 | 98.05 | 97.01 | 94.93 | 93.73 | 87.37 | 94 |
| SUL - 111 | 90.86 | 81.62 | 97.33 | 93.69 | 94.34 | 79.21 | 90 |
| SUL - 112 | 96.26 | 96.52 | 95.38 | 92.97 | 93.06 | 0.00 | 79 |
| SUL - 114 | 81.14 | 87.16 | 89.94 | 87.70 | 77.93 | 0.00 | 71 |
| SUL - 117 | 0.72 | 89.29 | 93.56 | 84.79 | 90.09 | 0.00 | 60 |
| SUL - 118 | 13.67 | 45.70 | 36.22 | 52.88 | 88.50 | 92.45 | 55 |
| SUL - 120 | 17.65 | 65.27 | 95.54 | 91.63 | 88.73 | 81.46 | 73 |
| SUL - 121 | 87.31 | 88.97 | 94.75 | 88.94 | 92.74 | 0.00 | 75 |
| SUL - 122 | 5.15 | 22.54 | 85.60 | 85.17 | 88.50 | 55.56 | 57 |
| SUL - 123 | 68.42 | 90.50 | 83.16 | 88.41 | 88.16 | 0.75 | 70 |
| SUL - 125 | 8.09 | 0.00 | 97.27 | 96.65 | 88.44 | 22.50 | 52 |
| SUL - 126 | 0.00 | 0.00 | 68.12 | 92.68 | 98.62 | 80.21 | 57 |
| SUL - 127 | 0.00 | 0.00 | 97.56 | 96.67 | 89.19 | 92.05 | 63 |
| SUL - 128 | 28.21 | 100.00 | 100.00 | 100.00 | 99.41 | 0.00 | 71 |
| SUL - 129 | 0.00 | 5.65 | 88.80 | 89.92 | 91.52 | 0.00 | 46 |
| SUL - 130 | 0.00 | 12.73 | 85.65 | 89.61 | 86.55 | 1.49 | 46 |
| SUL - 131 | 2.99 | 1.59 | 22.52 | 91.10 | 75.38 | 0.00 | 32 |
| SUL - 132 | 93.96 | 91.41 | 88.30 | 91.11 | 89.73 | 80.51 | 89 |
| SUL - 134 | 87.43 | 86.34 | 87.74 | 86.58 | 88.82 | 36.51 | 79 |
| SUL - 135 | 71.94 | 83.90 | 93.82 | 93.85 | 83.46 | 33.06 | 77 |
| SUL - 136 | 99.60 | 100.00 | 98.37 | 99.52 | 99.35 | 100.00 | 99 |
| SUL - 137 | 78.17 | 86.12 | 93.88 | 90.88 | 78.71 | 0.53 | 71 |
| SUL - 138 | 92.84 | 91.74 | 77.01 | 91.71 | 93.30 | 86.94 | 89 |
| SUL - 139 | 13.33 | 4.57 | 4.26 | 90.05 | 89.67 | 80.33 | 47 |
| SUL - 140 | 8.70 | 17.95 | 95.65 | 97.00 | 94.63 | 0.00 | 52 |
| SUL - 141 | 58.51 | 96.25 | 0.75 | 99.44 | 96.77 | 99.12 | 75 |
| SUL - 142 | 0.00 | 73.02 | 98.51 | 99.16 | 99.42 | 91.89 | 77 |
| SUL - 143 | 30.59 | 35.00 | 14.94 | 49.47 | 97.83 | 98.43 | 54 |
| SUL - 144 | 4.08 | 18.27 | 21.57 | 25.93 | 91.01 | 92.59 | 42 |
| SUL - 145 | 12.99 | 28.68 | 21.43 | 7.84 | 78.61 | 88.08 | 40 |
| SUL - 146 | 0.96 | 17.00 | 90.63 | 80.65 | 85.49 | 0.00 | 46 |
| DMSO | 0.00 | 0.54 | 0.62 | 0.00 | 0.00 | 0.00 | 0 |
| Control |  |  |  |  | 4.71 | 0.00 | 2 |

EXAMPLE 2: PRESERVATION OF SMAC CELLS

Rat smooth muscle aortic cells (SMAC cells) were cultured in DMEM cell culture medium (Life Technologies, 41965-052) supplemented with fetal calf serum, penicillin and streptomycin. Cells were placed in a 37° C. C02-regulated humidified incubator and were allowed to proliferate for 24 hours before commencing experiments. The compounds Sul 84, Sul 85, Sul 89, Sul 112, Sul 121, Sul 127, and Sul 136 were dissolved in DMSO to a final concentration of 100 mM. This solution was then dissolved in DMEM cell culture media and added to the cells at different concentrations, preincubated during 1 hour at 37° C. cooled down to 4° C. and kept at 4° C. during 24 h. The cells were rewarmed during 1 h until 37° C. and were tested. A Trypan blue test was performed, as described above for the HEK cells. In addition to this Trypan blue exclusion assay, an absorption assay was performed. The extend of Trypan blue absorption was used as an indication of the number of non-viable cells. Trypan blue was added to a 6-wells plate to a final concentration of 0.05% and cells were incubated at 37° C. for 5 minutes. Subsequently, excess dye was removed by carefully washing wells three times with cold PBS. After washing, 150 µL of 1% SDS was added to the wells to lyse the cells and free the trypan blue from any non-viable cells. Cell lysates were centrifuged and supernatant was subsequently transferred to a 96-wells plate. 1% SDS was used as a blank and absorption was measured at 595 nm. Cell death was expressed as a percentage of untreated 4° C. controls (100%).

FIG. 2 shows the results of a Trypan blue absorption assay to evaluate the amount of cells that survived the hypothermia and rewarming process. The viability of the SMAC cells was up to 90%. Sul 136 is a racemic mixture. Sul 141 and Sul 142 are the R and S isomer, respectively. The S enantiomer has a better effect than the R enantiomer or the racemic mixture, even at lower concentration.

EXAMPLE 3: PRESERVATION OF BLOOD PLATELETS

Collection Via PRP

PRP platelets were harvested and 2.1 ml was suspended in Poly Propylene tubes of 5 ml, closed with a stop.

Several compounds according to the invention were added to the blood platelets directly after preparing the PRP plasma and incubated during 10 minutes at 37° C. or 30 minutes at room temperature. The blood platelets with the compound were then stored at 4° C.

A control was stored under shaking conditions at room temperature. Another control was stored at 4° C. without the addition of a compound. The compounds that were added are those listed in table 3.

A sample was taken out of each tube after 264 hours after addition of the compound and tested as follows:

The color and coagulation properties were visually analysed.

The thrombocyte cells that survived were counted and it was evaluated whether the thrombocytes were aggregated.

It was evaluated if the thrombocytes still were able to function after stimulation by the addition of ADP or under influence of collagen in a 96 well plate.

The adhesion was evaluated, meaning the ability of the platelets to bind collagen in a 6 well plate preincubated with collagen.

Via an ELISA assay, it was evaluated whether thromboxane was secreted from the platelets. Thromboxane facilitates aggregation and is produced by activated blood platelets.

Table 3 provides an overview of the results of the addition of the compounds to the blood platelets and evaluates the aggregation of the thrombocytes after addition of the compound according to the invention and cooling until 4° C.

TABLE 3

| Name of compound (see also Table 1 for the iupac name) | Purity of compound | Final Concentration of compounds added to bloodplatelets | Aggregation of blood platelets after storage |
| --- | --- | --- | --- |
| SUL-100 | >95% | 30 mM | + |
| SUL-117 | 92% | 30 mM | + |
| SUL-118 | 100% | 30 mM | + |
| SUL-120 | 90% | 30 mM | + |
| SUL-121 | 90% | 30 mM | + |
| SUL-125 | 90% | 30 mM | + |
| SUL-126 | 90% | 30 mM | + |
| SUL-132 | 99.6% | 30 mM | + |
| SUL-136 | 94% | 30 mM | + |
| SUL-138 | 98.5% | 30 mM | + |
| SUL-139 | 90-99% | 30 mM | + |
| SUL-141 | 97% | 30 mM | + |
| SUL-142 | 91% | 30 mM | ++ |
| SUL-143 | 98% | 30 mM | + |
| SUL-144 | >90% | 30 mM | + |
| SUL-145 | 95% | 30 mM | + |

− means that most of the thrombocytes were aggregated
a + indicates that a few cells were still viable but some cells aggregated
a ++ indicates that almost all cells were viable Collection Via the Apheresis Method and PRP Platelets were obtained via standard plateletpheresis procedures either on Haemonetics (donor 2611811 and donor 2611855) or on Cobe instruments (donor 2611770). According the protocol all units would be obtained with plateletpheresis procedure with the Cobe instrument, but from the three donations two were not passing the blood bank quality control criteria. Nevertheless, all platelet donations have a similar concentration and a similar platelet quality. In none of the platelet concentrates clots were found.

The freshly harvested platelets are weighed on a balance and for sampling of platelet concentrate a small PVC bag was seal-docked to the main platelet concentrate bag. Standard homogenization of platelet concentrate has to be done with a roller before sampling.

300 µM suspension of Sul 136 is added with a procedure, which keeps the bag content sterile and the Sul 136 is kept in suspension by frequent whirling and stored at 37° C. before it is added to the freshly harvested platelets. The Sul 136 suspension is added to three platelet bags directly from the bag. After addition, the content of the platelet bag is gently mixed. After 2 hours the first sample is drawn with a seal-docked sample bag. The sample bag is disconnected by welding and from this sample bag the samples are taken for hematology analyzing, aggregometer tests and the flowcytometry tests. Swirling in the bag is reported by experience of the laboratory worker in the standard format. Platelets without Sul 136 put on a flatbed shaker and stored at room temperature were used as control. Another control is stored at 4° C. Platelet samples in which Sul 136 is added, are stored without shaking in a refrigerator at 4° C.

Samples are taken after 2, 24, 48, 96, 168, 216, 264 hours and are stored for 7 weeks.

The samples are measured as follows:
Annexin V Test:
On a Beckman Coulter FC 500 flow cytometer using the Roche Annexin-V FLUOS Staining Kit
Procedure:
A mix of 20 µl Annexin-V fluorescein from Roche kit into 1 ml incubation buffer was made and 20 µl propidium iodide solution was added. 2 ml of platelet concentrate was centrifuged on standard Eppendorf centrifuge and the supernatant was discarded.

1 ml PBS buffer was added and cell concentration was checked whether it was around 1.000.000. This was diluted 100 times with the prepared Annexin-V fluorescein and propidium iodide mix and incubated for 15 minutes. 500 µl incubation buffer from kit was added and cell analysis was made in a flowcytometer.
Platelet Activation with ADP and TRAP
Platelet activation was performed on a Beckman Coulter FC 500 flowcytometer using CD 41 PE, CD 62p FITC, IgG1 FITC/IgG1 PE antibodies of a Beckman Coulter kit.
Test Tube 1:
40 µl Dilution buffer was brought in about 15 minutes to 37° C.; 10 µl IgG FITC/IgG PE+10 µl CD41 PE was added and mixed with Vortex, incubated 5 min at room temperature; 1000 µl cold HBSS buffer was added; measurement in flowcytometer was performed.
Test Tube 2:
40 µl Dilution buffer was brought in about 15 minutes to 37° C.; 10 µl CD41 PE+5 µl CD62 FITC was added and mixed with Vortex, incubated during 5 min. at room temperature; 1000 µl cold HBSS buffer was added; measurement in flowcytometer was performed.
Test Tube 3:
36 µl Dilution buffer+4 µl ADP was brought in about 15 minutes to 37° C.; 10 µl CD41 PE+5 µl CD62 FITC was added and mixed with Vortex, incubated during 5 min. at room temperature; 1000 µl cold HBSS buffer was added; measurement in flowcytometer was performed.
Test Tube 4:
36 µl Dilution buffer+4 µl TRAP was brought in about 15 minutes to 37° C.; 10 µl CD41 PE+5 µl CD62 FITC was added and mixed with Vortex; incubateed during 5 min. at room temperature; 1000 µl cold HBSS buffer was added; measurement in flowcytometer was performed.
Platelet aggregation was measured according to Platelet Aggregation Profiler PAP 8 (Mölab) using all reagents from Mölab.
Sample Preparation:
3 ml platelet concentrate was centrifuged at 3000 RPM to get PPP. 1800 µl PPP and 600 µl PRP were mixed.
Test:
225 µl PRP was brought in test tube with magnetic stirrer. 225 µl PPP+25 µl aquadest was brought in test tube without magnetic stirrer. PPP was used for basis. PRP was put during 2 min at 37° C. on a roller. Measurement with PRP in aggregometer was started after 30 seconds with 25 µl inductor. Measurement was performed during 6 min.
Visual determination of swirling was performed according to Bertolini, F. and Murphy, S. (1994) (A multicenter evaluation of reproducibility of swirling in platelet concentrates, Transfusion 34, 796-801.)
Results of Tests with PRP Collected Platelets
PRP platelets were tested with the addition of Sul 136. Table 4 shows the results of the number cells that survived 24, 48, 72, and 216 hours after storage at 4° C. The number of cells are given in % relative to the number of cells at time 0. 66% of the platelets stored at room temperature survived after 216 hours. Only 42.3% of the cells stored at 4° C. survived after 216 hours. The addition of Sul 136 resulted that substantial more platelets survived after storage of 72 and 216 hours at 4° C.

TABLE 4

| Sample | Time in hours | | |
|---|---|---|---|
| | 0 | 72 | 216 |
| PRP Room Temp | 100 | 80.7 | 66.1 |
| PRP 4° C. | 100 | 43.3 | 42.3 |
| 60 min 0.001 mM | 100 | 83.8 | 86.1 |
| 60 min 0.01 mM | 100 | 82.9 | 94.8 |
| 60 min 0.1 mM | 100 | 76.3 | 77.6 |
| 60 min 1 mM | 100 | 29.9 | 62.9 |
| 60 min 10 mM | 100 | 51.8 | 43.4 |
| 10 min 0.001 mM | 100 | 58.9 | 55.1 |
| 10 min 0.01 mM | 100 | 66.0 | 52.1 |
| 10 min 0.1 mM | 100 | 55.9 | 50.8 |
| 10 min 1 mM | 100 | 59.1 | 59.3 |
| 10 min 10 mM | 100 | 64.8 | 47.9 |

Table 5 shows the possibility of aggregation of the platelets collected with PRP and where Sul 136 was added, after stimulation with ADP. When 10 mM Sul 136 was added, the platelets still showed activity after stimulation with ADP. (+means that the cells show aggregation and can thus be activated upon stimulation, −means no aggregation upon stimulation)

TABLE 5

| Sample | 0 h | 24 h | 48 h | 72 h | 216 h |
|---|---|---|---|---|---|
| PRP KT | + | + | + | − | − |
| PRP 4° C. | + | − | − | − | − |
| 60 min 0.001 mM | + | − | − | − | − |
| 60 min 0.01 mM | + | − | − | − | − |
| 60 min 0.1 mM | + | − | − | − | − |
| 60 min 1 mM | + | − | − | − | − |
| 60 min 10 mM | + | + | + | + | − |
| 10 min 0.001 mM | + | − | − | − | − |
| 10 min 0.01 mM | + | − | − | − | − |
| 10 min 0.1 mM | + | − | − | − | − |
| 10 min 1 mM | + | − | − | − | − |
| 10 min 10 mM | + | + | + | + | + |

Table 6 shows the possibility of aggregation of the PRP platelets with Sul 136 after stimulation with collagen. When 10 mM Sul 136 was added, the platelets showed still activity after stimulation with collagen. (+means that the cells show aggregation, ++means strong aggregation, these platelets can thus be activated upon stimulation, −means no aggregation upon stimulation)

TABLE 6

| Sample | 0 h | 24 h | 48 h | 72 h | 216 h |
|---|---|---|---|---|---|
| PRP KT | + | + | + | − | − |
| PRP 4° C. | + | − | − | − | − |
| 60 min 0.001 mM | + | − | − | − | − |
| 60 min 0.01 mM | + | − | − | − | − |
| 60 min 0.1 mM | + | − | − | − | − |
| 60 min 1 mM | + | − | − | − | − |
| 60 min 10 mM | ++ | ++ | ++ | ++ | − |
| 10 min 0.001 mM | + | − | − | − | − |
| 10 min 0.01 mM | + | − | − | − | − |
| 10 min 0.1 mM | + | − | − | − | − |
| 10 min 1 mM | + | − | − | − | − |
| 10 min 10 mM | ++ | ++ | ++ | ++ | ++ |

Results with Platelet Collected Via Apheresis

Table 7 shows the results of the test of the stored apherese blood platelets of donor 1(2611770) stored at room temperature on a flatbed shaker without Sul 136. The pH at day 12 was 6.3. The pH at day 19 was 5.7

Table 8 shows the results of the tests of the stored apherese blood platelets of donor 1, stored at 4° C. with the addition of Sul 136. The pH on day 12 was 6.2, the pH on day 19 was 5.9.

TABLE 7

| | | | Platelet aggregation | | Flow cytometry | | | |
|---|---|---|---|---|---|---|---|---|
| Date | Platelets/μl | MPV fL | Collagen (%) | ADP (%) | P-selectin MFI | ADP | TRAP | Annexin (% positive) |
| Day 1 | 1,316,000 | 8.2 | 35 | 10 | 1.99 | 6.54 | 12.8 | 3.13 |
| Day 2 | 1,248,000 | 9.7 | 72 | 0 | 2.09 | 3.97 | 12.3 | 5.15 |
| Day 3 | 1,400,000 | 9.0 | 27 | 0 | 2.17 | 4.00 | 11.7 | 5.72 |
| Day 5 | 1,212,000 | 9.6 | 0 | 0 | 3.21 | 4.09 | 12.6 | 6.41 |
| Day 8 | 1,216,000 | 9.6 | 0 | 0 | 3.47 | 4.53 | 10.2 | 16.70 |
| Day 10 | 1,324,000 | 8.8 | 0 | 0 | 3.00 | 3.82 | 7.85 | 14.22 |
| Day 12 | 1,528,000 | 9.2 | 0 | 0 | 4.34 | 4.78 | 6.51 | 21.45 |
| Day 19 | 1,328,000 | 9.0 | 0 | 0 | 3.89 | 3.74 | 3.67 | 84.53 |

TABLE 8

| | | | Platelet aggregation | | Flow cytometry | | | |
|---|---|---|---|---|---|---|---|---|
| Date | Platelets/μl | MPV fL | Collagen (%) | ADP (%) | P-selectin MFI | ADP | TRAP | Annexin (% positive) |
| Day 1 | 1,000,000 | 10.6 | 0 | 0 | 2.09 | 3.07 | 3.57 | 4.51 |
| Day 2 | 1,192,000 | 9.5 | 0 | 0 | 3.04 | 3.28 | 3.78 | 14.48 |
| Day 3 | 1,240,000 | 9.2 | 0 | 0 | 3.73 | 4.12 | 4.95 | 18.24 |
| Day 5 | 1,232,000 | 9.1 | 0 | 0 | 4.12 | 4.20 | 5.55 | 20.38 |

TABLE 8-continued

| Date | Platelets/μl | MPV fL | Platelet aggregation Collagen (%) | ADP (%) | Flow cytometry P-selectin MFI | ADP | TRAP | Annexin (% positive) |
|---|---|---|---|---|---|---|---|---|
| Day 8 | 1,352,000 | 9.3 | 0 | 0 | 4.82 | 4.83 | 5.52 | 34.56 |
| Day 10 | 1,228,000 | 9.6 | 0 | 0 | 4.48 | 4.46 | 5.52 | 43.52 |
| Day 12 | 1,204,000 | 9.8 | 17 | 12 | 4.57 | 4.43 | 4.42 | 56.91 |
| Day 19 | 1,068,000 | 8.8 | 32 | 31 | 2.92 | 2.74 | 2.76 | 88.34 |

The flow cytometry tests were similar for the platelets stored at room temperature and the platelets stored at 4° C. with compound Sul 136. Moreover, the platelet aggregation upon stimulation with collagen and ADP was restored at day 12 and day 19 for platelets stored with compound Sul 136.

This result is comparable with the platelets stored at room temperature at day 1-3.

Table 9 and 10 show the results of the test performed with platelets form Donor 2. The platelets from table 9 were stored at 4° C. without Sul 136. The platelets from table 10 were stored at 4° C. with Sul 136.

TABLE 9

| Date | Platelets/μl | MPV fL | Platelet aggregation Collagen (%) | ADP (%) | Flow cytometry P-selectin MFI | ADP | TRAP | Annexin (% positive) |
|---|---|---|---|---|---|---|---|---|
| Day 1 | 1,008,000 | 7.8 | 89 | 15 | 1.82 | 4.67 | 7.83 | 3.89 |
| Day 2 | 792,000 | 6.5 | 83 | 36 | 2.50 | 5.62 | 7.18 | 10.83 |
| Day 3 | 632,000 | 6.3 | 86 | 22 | 2.76 | 5.51 | 5.87 | 17.92 |
| Day 5 | 824,000 | 6.5 | 82 | 27 | 3.43 | 6.44 | 7.30 | 24.04 |
| Day 8 | 816,000 | 6.5 | 77 | 19 | 3.35 | 5.28 | 7.12 | 22.52 |
| Day 10 | 684,000 | 6.5 | 83 | 13 | 3.00 | 4.12 | 5.13 | 22.78 |
| Day 12 | 732,000 | 6.5 | 75 | 12 | 2.93 | 3.92 | 5.15 | 28.12 |
| Day 19 | 868,000 | 6.5 | 24 | 9 | 2.81 | 2.90 | 3.54 | 34.18 |

TABLE 10

| Date | Platelets/μl | MPV fL | Platelet aggregation Collagen (%) | ADP (%) | Flow cytometry P-selectin MFI | ADP | TRAP | Annexin (% positive) |
|---|---|---|---|---|---|---|---|---|
| Day 1 | 1,004,000 | 10.1 | 0 | 0 | 1.67 | 2.12 | 1.88 | 5.98 |
| Day 2 | 1,272,000 | 7.6 | 0 | 0 | 2.13 | 2.53 | 2.35 | 10.96 |
| Day 3 | 1,220,000 | 7.8 | 4 | 0 | 2.59 | 3.21 | 2.76 | 19.56 |
| Day 5 | 1,252,000 | 8.0 | 0 | 0 | 2.95 | 3.19 | 3.16 | 32.11 |
| Day 8 | 1,168,000 | 8.0 | 0 | 0 | 2.99 | 3.08 | 3.22 | 45.71 |
| Day 10 | 1,104,000 | 8.1 | 0 | 0 | 2.76 | 2.83 | 2.96 | 53.96 |
| Day 12 | 1,032,000 | 8.6 | 5 | 0 | 2.63 | 2.62 | 2.73 | 62.97 |
| Day 19 | 860,000 | 8.8 | 0 | 0 | 2.01 | 1.99 | 2.14 | 72.67 |

Table 11 and 12 show the results of the test performed with platelets from Donor 3. The platelets from table 9 were stored at room temperature without Sul 136. The platelets from table 10 were stored at 4° C. with Sul 136.

TABLE 11

| Date | Platelets/μl | MPV fL | Platelet aggregation Collagen (%) | ADP (%) | Flow cytometry P-selectin MFI | ADP | TRAP | Annexin (% positive) |
|---|---|---|---|---|---|---|---|---|
| Day 1 | 1,060,000 | 7.7 | 80 | 9 | 2.10 | 6.09 | 10.80 | 3.69 |
| Day 2 | 1,004,000 | 9.6 | 81 | 0 | 2.18 | 3.81 | 9.20 | 3.87 |
| Day 3 | 1,060,000 | 7.6 | 75 | 0 | 2.34 | 3.74 | 9.48 | 5.21 |
| Day 5 | 964,000 | 10.1 | 34 | 0 | 2.80 | 4.29 | 10.80 | 6.12 |

TABLE 11-continued

| Date | Platelets/μl | MPV fL | Platelet aggregation | | Flow cytometry | | | Annexin (% positive) |
|---|---|---|---|---|---|---|---|---|
| | | | Collagen (%) | ADP (%) | P-selectin MFI | ADP | TRAP | |
| Day 8 | 956,000 | 9.6 | 72 | 0 | 3.55 | 4.70 | 11.30 | 5.38 |
| Day 10 | 976,000 | 9.3 | 23 | 0 | 3.30 | 4.36 | 8.44 | 8.09 |
| Day 12 | 1,068,000 | 9.2 | 41 | 0 | 3.67 | 4.85 | 7.39 | 14.08 |
| Day 19 | 1,028,000 | 9.7 | 0 | 0 | 4.76 | 4.56 | 4.59 | 90.52 |

TABLE 12

| Date | Platelets/μl | MPV fL | Platelet aggregation | | Flow cytometry | | | Annexin (% positive) |
|---|---|---|---|---|---|---|---|---|
| | | | Collagen (%) | ADP (%) | P-selectin MFI | ADP | TRAP | |
| Day 1 | 980,000 | 10.3 | 0 | 0 | 1.90 | 2.71 | 2.08 | 5.14 |
| Day 2 | 1,188,000 | 7.7 | 0 | 0 | 2.82 | 3.49 | 3.62 | 8.68 |
| Day 3 | 1,072,000 | 7.7 | 0 | 0 | 3.84 | 4.96 | 4.42 | 14.34 |
| Day 5 | 1,068,000 | 8.0 | 0 | 6 | 4.50 | 4.84 | 5.04 | 27.77 |
| Day 8 | 992,000 | 8.3 | 0 | 0 | 4.82 | 4.91 | 5.24 | 41.97 |
| Day 10 | 892,000 | 8.3 | 0 | 0 | 4.37 | 4.25 | 5.04 | 62.65 |
| Day 12 | 912,000 | 9.0 | 8 | 0 | 3.89 | 3.84 | 4.20 | 70.33 |
| Day 19 | 692,000 | 9.5 | 0 | 0 | 2.22 | 2.37 | 2.01 | 80.99 |

Swirling Test

Still after 7 weeks Swirling is observed in the platelets stored with the compounds at 4 C Swirling is not observed at platelets without added compounds stored at 4 C, measured after 24 hours.

EXAMPLE 4: SYNTHESIS OF THE COMPOUNDS

The compounds according to the invention are synthesized according to standard synthesis methods which are well known by a person skilled in the art.

SUL-0083, SUL-0084 and SUL-0085 are commercially available.

Synthesis of SUL 089-112, 114-117, 120-126, 128-130, 132, 134-135, 138, and 140.

Amidation of trolox was achieved by reaction with the appropriate amine in the presence of standard coupling reagents for amide formation, e.g., HATU and CDI. The corresponding amines were prepared by reduction of the amides formed with $BH_3$ Hydroxamic acid derivatives were prepared by reaction with hydroxylamine/CDI. The synthesis of carbohydrazide analogues of trolox was achieved by reaction with (substituted) hydrazines. Enantiomeric/diastereomeric compounds were prepared starting from enantiomerically pure (R)- or (S)-Trolox or by means of chiral chromatography.

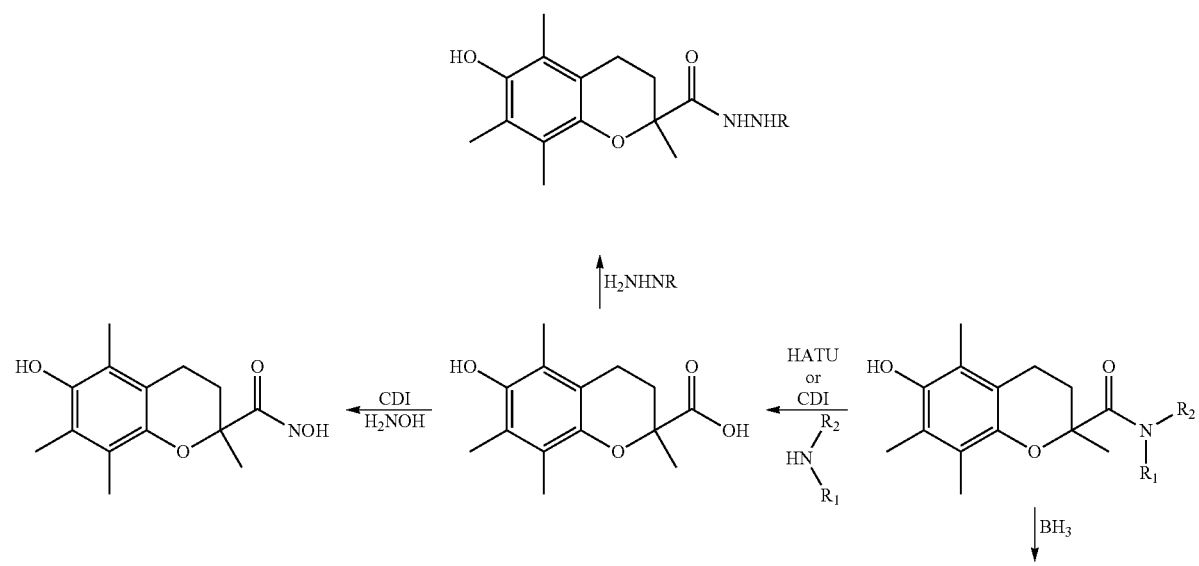

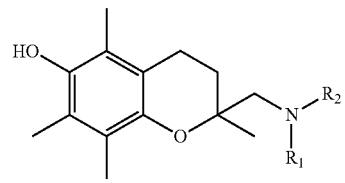

Synthesis of SUL-118, SUL-119 en SUL-146

Oxidation of commercially available propofol with salcomine, a coordination complex of the salen ligand with cobalt, followed by reduction with NaBH$_4$ afforded 2,6-diisopropylbenzene-1,4-diol Subsequent methylation with HCO/SnCl$_2$/HCl and reaction with methyl methacrylate furnished SUL-146 (methyl 6-hydroxy-5,7-diisopropyl-2,8-dimethylchroman-2-carboxylate). Hydrolysis with LiOH yielded the carboxylic acid SUL-118 (6-hydroxy-5,7-diisopropyl-2,8-dimethylchroman-2-carboxylic acid). The alcohol SUL-119 (2-(hydroxymethyl)-5,7-diisopropyl-2,8-dimethylchroman-6-ol) was obtained by reduction of SUL-146 with LiAlH$_4$.

Synthesis of SUL-131, SUL-133, SUL 137 en SUL-146

Starting from the carboxylic acid SUL-118 (6-hydroxy-5,7-diisopropyl-2,8-dimethylchroman-2-carboxylic acid), the hydroxylamine was obtained by reaction with hydroxylamine using CDI as coupling reagent. Compounds SUL 133 ((6-hydroxy-5,7-diisopropyl-2,8-dimethylchroman-2-yl) (4-(2-hydroxyethyl)piperazin-1-yl)methanone) and SUL 137 ((6-hydroxy-5,7-diisopropyl-2,8-dimethylchroman-2-yl) (piperazin-1-yl)methanone) were prepared by reaction of SUL-118 with the appropriate piperazine derivative. Both coupling reagents HATU and CDI resulted in satisfactorily yields. SUL 139 (2-(4-(6-hydroxy-5,7-diisopropyl-2,8-dimethylchroman-2-carbonyl)piperazin-1-yl)acetic acid) was prepared by a reductive amination of SUL 137 ((6-hydroxy-5,7-diisopropyl-2,8-dimethylchroman-2-yl) (piperazin-1-yl)methanone) with glyoxalic acid.

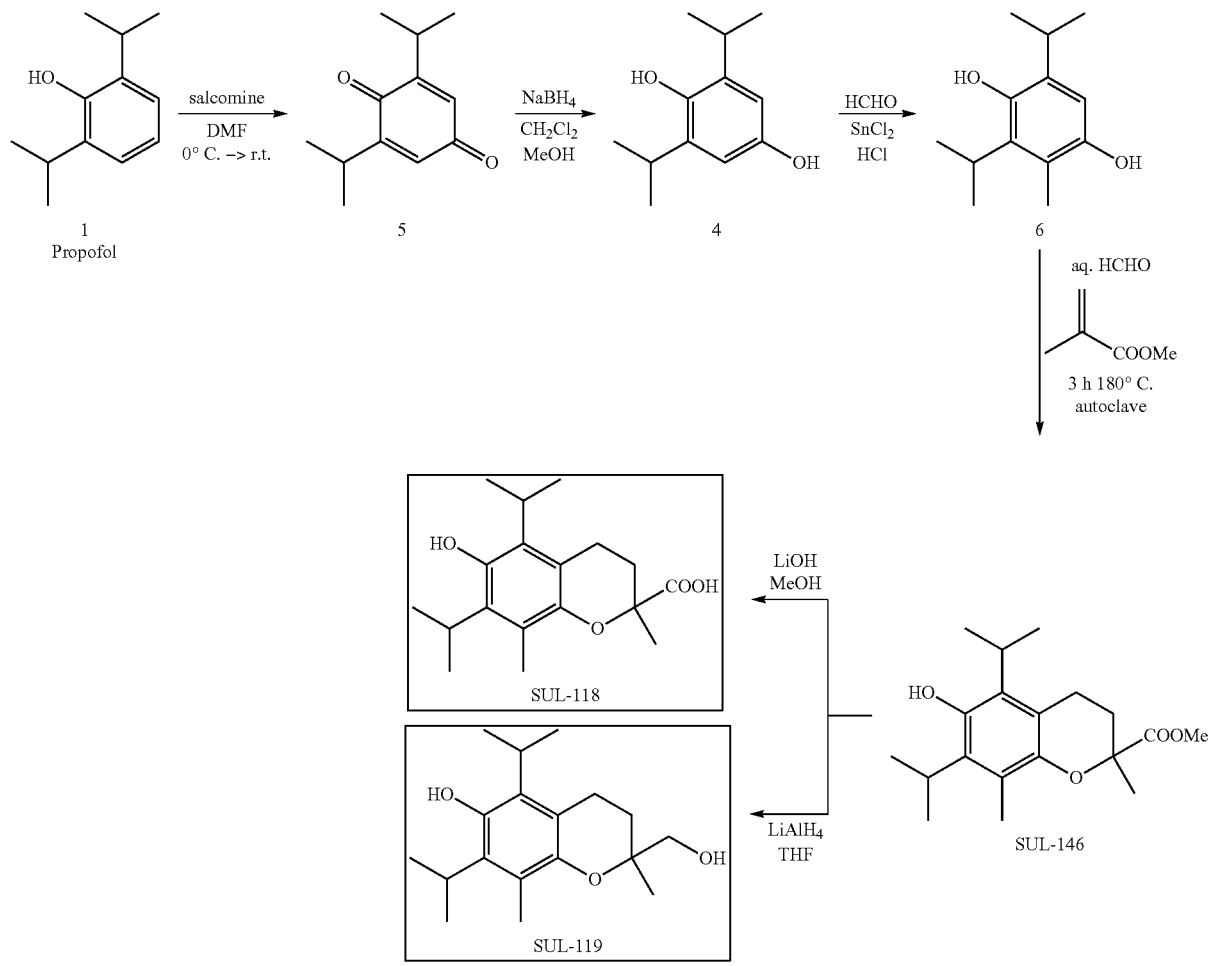

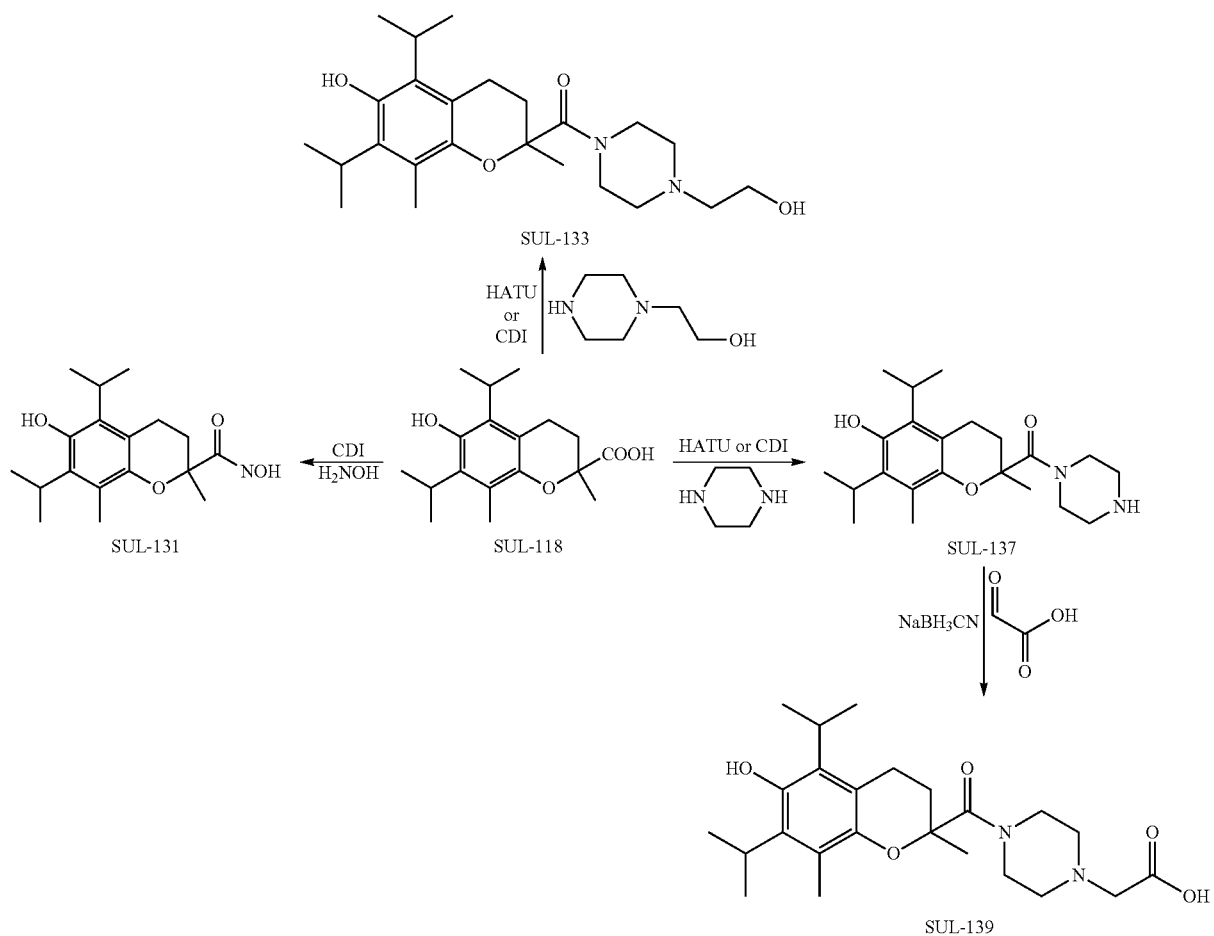

Synthesis of SUL-136, SUL-141 and SUL-142.

Hydrolysis of SUL-140 (ethyl 2-(4-(6-hydroxy-2,5,7,8-tetramethylchroman-2-carbonyl)piperazin-1-yl)acetate) under N, atmosphere furnished SUL-136 (2-(4-(6-hydroxy-2,5,7,8-tetramethylchroman-2-carbonyl)piperazin-1-yl)acetic acid) in high yield. The enantiomers SUL-141 and SUL-142 were prepared according to the above-described conditions.

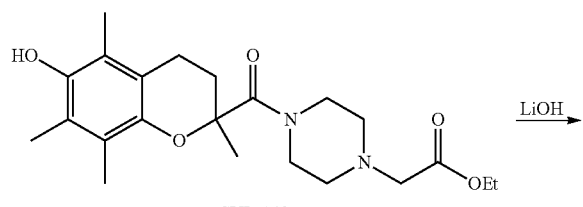

Synthesis of SUL 143, 144 en 145

Amidation of trolox with (S)-methyl pyrrolidine-2-carboxylate (L-proline methyl ester) afforded, after column chromatography, two diastereoisomers. Subsequent hydrolysis of the individual diastereoisomers afforded SUL-144 ((2S)-1-(6-hydroxy-2,5,7,8-tetramethylchroman-2-carbonyl)pyrrolidine-2-carboxylic acid, diastereomer 1) and SUL-145 ((2S)-1-(6-hydroxy-2,5,7,8-tetramethylchroman-2-carbonyl)pyrrolidine-2-carboxylic acid, diastereomer 2). The racemic analogue SUL-143 ((2S)-1-(6-hydroxy-2,5,7,8-tetramethylchroman-2-carbonyl)pyrrolidine-2-carboxylic acid) was obtained by mixing the esters of the individual diastereoisomers followed by hydrolysis of the ester moiety using LiOH.

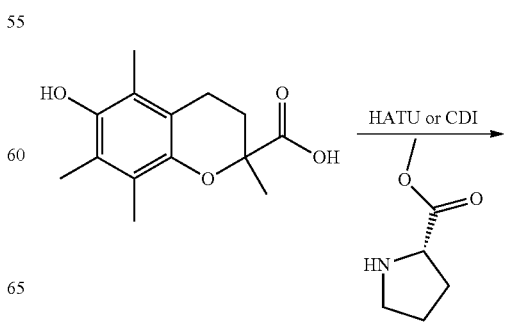

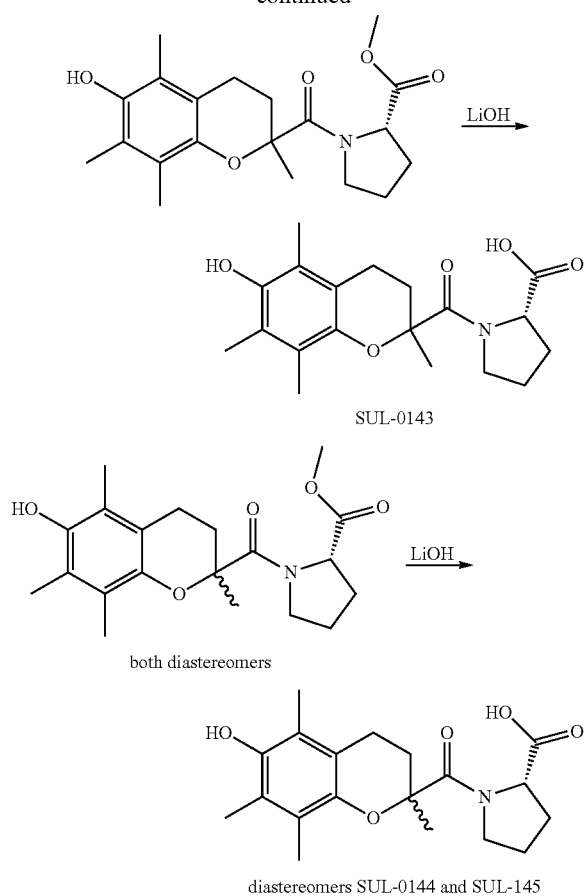

both diastereomers diastereomers SUL-0144 and SUL-145

Amidation of Trolox (General Example)

SUL-108 ((4-butylpiperazin-1-yl) (6-hydroxy-2,5,7,8-tetramethylchroman-2-yl)methanone)

HCl. Trolox (11 g, 0.044 mol, 1 eq.) was suspended in acetonitrile (100-150 ml). CDI (8.6 g, 0.053 mol, 1.2 eq.) was added in portions. The reaction mixture was stirred for 0.5-1 hour at room temperature. After addition of 1-butylpiperazine (6.9 g, 0.048 mol, 1.1 eq.) the reaction mixture was stirred at 25-30° C. over the weekend. The reaction mixture was concentrated, H$_2$O (200 ml) was added and the aqueous layer was extracted with EtOAc (4×). The combined organic layers were dried, filtered and concentrated. The crude product obtained was purified by column chromatography (DCM/10% MeOH) affording the compound aimed for (9 g product, 82% pure). Crystallization from EtOAc/heptanes afforded SUL-108 (6 g, 0.016 mol, 36% yield, 90% pure) as a white solid. The material obtained was dissolved in DCM (50-100 ml). HCl (4 M in dioxane, 8.8 ml, 0.0035 mol, 2.2 eq.) was added and the reaction mixture was stirred at room temperature over the weekend. The mixture was filtered, rinsed with DCM, and dried to afford the HCl salt of SUL-108 (6.3 g, 97-98% pure) as a white solid.

$^1$H-NMR (CDCl$_3$, in ppm): 0.93 (t, 3H), 1.38 (m, 2H), 1.58 (s, 3H), 1.67 (m, 2H), 2.09 (s, 3H), 2.12 (s, 3H), 2.15 (s, 3H), 2.50-3.20 (m, 14H). M$^+$=375.3

Reduction of Trolox Amides (General Example)

SUL-128. (2-(((S)-2-(hydroxymethyl)pyrrolidin-1-yl)methyl)-2,5,7,8-tetramethylchroman-6-ol)

HCl. BH$_3$.THF in THF (16 ml, 0.0156 mol, 2 eq.) was cooled to T=0° C. A solution of SUL-112 ((6-hydroxy-2,5,7,8-tetramethylchroman-2-yl)((S)-2-(hydroxymethyl)pyrrolidin-1-yl)methanone; 2.6 g, 0.0078 mol, 1 eq.) in THF (50 ml) was added drop-wise and the reaction mixture was refluxed for 1 hour and cooled to room temperature overnight. The reaction mixture was cooled on an ice bath and HCl (6 M, 25 ml) was added drop-wise. DCM (100 ml) was added and the layers were separated. The aqueous layer was extracted with DCM (3×). The combined org. layers were dried over K$_2$CO$_3$ until no gas formation was noticed anymore. The organic phase was filtered and concentrated. The crude product was cooled on an ice bath, and NaOH (6M, 50 ml) was added drop-wise. After addition the reaction mixture was stirred for 1 hour and extracted with DCM (4×). The combined DCM layers were dried, filtered and concentrated to give 1.6 g crude product (20-40% pure). The material was purified by column chromatography affording SUL-128 (300 mg, 0.94 mmol, 12% yield, 90% pure). This was dissolved in DCM (10 ml) and cooled to T=0° C. (ice bath). HCl (4M in dioxane, 0.3 ml, 0.94 mmol, 1.2 eq.) was added and the reaction mixture was stirred at room temperature overnight. The solid formed was filtered, washed with Et$_2$O and dried to afford the HCl salt of SUL-128 (300 mg, 90% pure) as a white solid (mixture of diastereomers).

$^1$H-NMR (CDCl$_3$, in ppm): 1.20-1.90 (m, 7H), 2.12 (s, 6H), 2.17 (s, 3H), 2.20-2.90 (m, 9H), 3.4-3.65 (m, 2H). M$^+$=320.1

Synthesis of SUL-118 (6-hydroxy-5,7-diisopropyl-2,8-dimethylchroman-2-carboxylic acid)

Synthesis of 2,6-Diisopropylcyclohexa-2,5-diene-1,4-dione

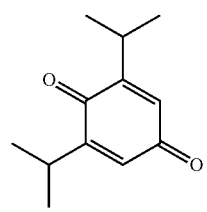

Propofol 100 g, 561 mmol) was dissolved in DMF (250 mL). The solution was cooled to 0° C. while stirring. Salcomine (16.6 g, 51 mmol; 9 mol %) was added and the resulting reaction mixture was stirred 112 h overnight while warming to room temperature. The reaction mixture was poured in water (7 L). The resulting slurry was extracted with heptanes (5×1 L). The combined organic extracts were dried with Na$_2$SO$_4$. Concentration of the solution under vacuum afforded the crude 2,6-diisopropylcyclohexa-2,5-diene-1,4-dione (62.5 g; 325 mmol; 58% yield) as an oil. The product was used in the next step without further purification.

Synthesis of 2,6-Diisopropylbenzene-1,4-diol

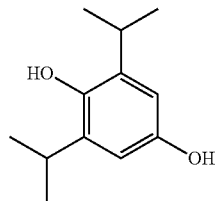

Crude 2,6-diisopropylcyclohexa-2,5-diene-1,4-dione (62.5 g, 325 mmol) was dissolved in dichloromethane (300 mL) and methanol (100 mL). The solution was cooled to 0° C. with an ice bath. Sodium borohydride (4.5 g, 182 mmol) was added in portions. After the addition was complete the reaction mixture was stirred at room temperature overnight. Acetone (150 mL) was added to quench the excess of sodium borohydride. After 30 minutes stirring 2N aq. HCl (200 mL) was added. After stirring for 45 minutes the mixture was extracted with ethyl acetate (4×400 mL). The combined organic layers were dried with $Na_2SO_4$. Concentration of the solution under vacuum afforded crude 2,6-diisopropylbenzene-1,4-diol (64 g, 330 mmol) as a red oil in quantitative yield. The product was used in the next step without further purification.

Synthesis of 3,5-Diisopropyl-2-methylbenzene-1,4-diol

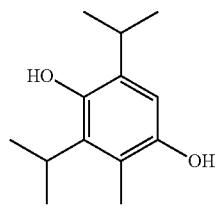

A mixture of 2,6-diisopropylbenzene-1,4-diol (64 g, 0.33 mol), paraformaldehyde (9.8 g, 0.327 mol), $SnCl_2$ (217.9 g, 1.15 mol), concentrated aq. 37% HCl (0.6 L) and diisopropyl ether (2.5 L) was heated to reflux for 4 hours. After cooling to room temperature overnight the biphasic mixture was separated. The aqueous layer was extracted with TBME (2000 mL). The combined organic fractions were washed with 1N aq. HCl (1000 mL), water (1000 mL) and brine (1000 mL). The organic fractions were dried with $Na_2SO_4$ and concentrated under vacuum to give a 50:35 mixture of 3,5-diisopropyl-2-methylbenzene-1,4-diol and 2,6-diisopropyl-3,5-dimethylbenzene-1,4-diol (61 g oil) according to GCMS analysis. Purification by chromatography on silica gel (1200 mL) eluting with ethyl acetate/heptanes=97.5:2.5 (4000 mL), 95:5 (4000 mL) gave 3,5-diisopropyl-2-methylbenzene-1,4-diol 6 (16.6 g, 79.8 mmol; 24%; 83% pure) as an oil.

Synthesis of Methyl 6-hydroxy-5,7-diisopropyl-2,8-dimethylchroman-2-carboxylate

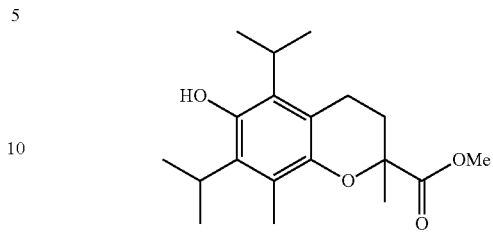

3,5-diisopropyl-2-methylbenzene-1,4-diol (10.6 g, 50.9 mmol; 83% pure) was dissolved in methyl methacrylate (20 mL, 186 mmol). The solution was transferred to a Teflon tube in a Berghof reactor. Aqueous formaldehyde (10 mL; 37% wt. solution, stabilized with 10-15% MeOH) was added and the reaction mixture was heated to 180° C. (internal temperature) in the closed reactor for 5 hours while stirring. After cooling to ca. 40° C. The reaction mixture was poured in MeOH (200 mL) and the mixture was concentrated under vacuum. Purification by chromatography on silica gel (600 mL) eluting with ethyl acetate/heptanes=95:5 (5000 mL; TLC: Rf~0.2; spot stained with iodine vapor) gave the desired pure product methyl 6-hydroxy-5,7-diisopropyl-2,8-dimethylchroman-2-carboxylate (10.0 g, 31.3 mmol, 61%).

Synthesis of 6-Hydroxy-5,7-diisopropyl-2,8-dimethylchroman-2-carboxylic acid (SUL-118)

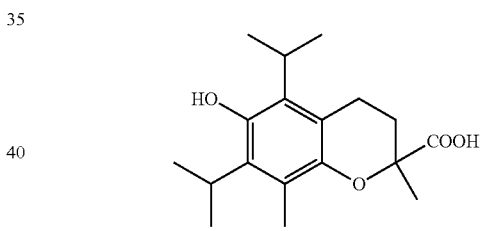

A mixture of purified methyl 6-hydroxy-5,7-diisopropyl-2,8-dimethylchroman-2-carboxylate (8.3 g, 25.9 mmol) and lithium hydroxide monohydrate (4.3 g, 102.5 mmol; 4 eq.) in MeOH (100 mL), THF (100 mL) and water (25 mL) was heated for 30 minutes at ambient pressure while rotating with a rotary evaporator in a warm water bath at 60° C. The organic solvents were evaporated under vacuum. Water (150 mL) was added to the residue, followed by acetic acid (10 mL). A light orange mixture was obtained. Extraction with ethyl acetate (3×100 mL), drying of the combined organic fractions with $Na_2SO_4$ and concentration under vacuum gave the crude product as an orange solid. The solids were stirred with tBME (150 mL). A beige solid precipitated and an orange solution was obtained. Heptane (250 mL) was added and the mixture was stirred for 15 minutes. The mixture was filtered over a glass filter. The residual solids were washed with heptanes (2×50 mL) on the filter under suction. Drying of the solids under vacuum at 60° C. gave pure 6-hydroxy-5,7-diisopropyl-2,8-dimethylchroman-2-carboxylic acid (SUL-118) as an off-white solid (3.1 g, 10.13 mmol; 39%, 100% pure). $^1$H-NMR ($CDCl_3$, in ppm): 1.38 (t, 12H), 1.52 (s, 3H), 1.87 (m, 1H), 2.20 (s, 3H), 2.30 (m, 1H), 3.20 (m, 1H), 3.38 (m, 1H). M+=307.10

EXAMPLE 5. SYNTHESIS OF SUL 119 (2-(HYDROXYMETHYL)-5,7-DIISOPROPYL-2,8-DIMETHYLCHROMAN-6-OL)

A solution of methyl 6-hydroxy-5,7-diisopropyl-2,8-dimethylchroman-2-carboxylate (500 mg, 1.56 mmol) in THF (12 mL) was added over 5 minutes with a syringe via a rubber septum to $LiAlH_4$ (238 mg, 6.26 mmol; 4 eq.), pre-weighed in a dry 3-mecked 100 mL round bottomed flask under inert nitrogen atmosphere while stirring at room temperature. The exothermic addition of the ester was accompanied with gas evolution. After the addition was complete the resulting grey suspension was heated to reflux. After 3 hours the heating was stopped and the reaction was quenched by dropwise addition of EtOAc (6 mL; exothermic). Water (5 mL) was added in small portions, followed by 2N HCl (2 mL) followed by EtOAc (25 mL). The mixture was poured on $Na_2SO_4$ (ca. 50 g) and the slightly yellow organic layer was separated from the two-phase mixture. The aqueous phase was washed with EtOAc (50 mL) and the combined organic fractions were concentrated under vacuum to give the crude alcohol (530 mg) as a clear oil. Heptane (100 mL) was added and after concentration under vacuum the 2-(hydroxymethyl)-5,7-diisopropyl-2,8-dimethylchroman-6-ol (248 mg, 0.85 mmol, 54%, LCMS: 95.5% pure).

M+=293.2

EXAMPLE 6. SYNTHESIS OF SUL 139 (2-(4-(6-HYDROXY-5,7-DIISOPROPYL-2,8-DIMETHYL-CHROMAN-2-CARBONYL)PIPERAZIN-1-YL)ACETIC ACID)

SUL-137 (440 mg, 1.17 mmol, 1 eq.) was dissolved in MeOH (50 ml) and glyoxalic acid (216 mg, 2.35 mmol, 2 eq.) was added. The resulting mixture was stirred for 1 hour at room temperature and, subsequently, $NaBH_3CN$ (183 mg, 2.94 mmol, 2.5 eq.) was added. The reaction mixture was stirred at room temperature overnight. Acetic acid (few ml) was added and after stirring at room temperature for 0.5-1 hour, the reaction mixture was concentrated. The residue obtained was dissolved in EtOAc, washed with $H_2O$ (2×), dried, filtered and concentrated to afford SUL-139 (500 mg, 1.16 mmol, 98%, 91-92% pure) as a light yellow solid.

$^1$H-NMR ($CD_3OD$, in ppm): 1.33 (dd, 12H), 1.59 (s, 3H), 1.62 (m, 1H), 2.09 (s, 3H), 2-5-3.0 (m, 7H), 3.1-3.6 (m, 4H), 3.81 (bs, 2H), 4.28 (bs, 2H). M$^+$=433.2.

EXAMPLE 7. SYNTHESIS OF SUL 136 (2-(4-(6-HYDROXY-2,5,7,8-TETRAMETHYLCHROMAN-2-CARBONYL)PIPERAZIN-1-YL)ACETIC ACID)

A 250 ml three-necked flask equipped with two septa (left and right) and a stopcock was charged with SUL-136 (15.5 g, 38.4 mmol) and THF/water (240 ml THF+80 ml water). The clear solution was stirred and degassed for at least 30 minutes by argon-bubbling, using an inlet tube equipped with a long syringe needle through the left septum; the right septum was equipped with a short needle and functioned as outlet. The degassed solution (which was maintained under argon) was cooled to 0° C. in an ice-bath and solid anhydrous LiOH (2.3 g, 96 mmol, 2.5 eq.) was added in one portion. The resulting reaction mixture was stirred for 2 hours at 0° C. after which is was neutralized by addition of a MeOH/water (3/1, v/v) slurry of Dowex-50WX8-200 ion-exchange resin; the final pH was approx 6. The Dowex resin was filtered off with suction and rinsed with 3 portions of MeOH/water (3/1, v/v). The filtrate was reduced in vacuo and to the wet product was added approx. 100 ml water. The resulting white aqueous suspension was freeze-dried overnight to afford SUL-136 (13.48 g, 93%. LCMS: 99.6%) as a white solid. 1H-NMR (CD3OD, in ppm)): 1.60 (s, 3H), 1.65 (m, 1H), 2.05 (s, 3H), 2.10 (s, 6H), 2.55 (m, 2H), 2.62 (m, 1H), 3.0, (bs, 4H), 3.40 (bs, 2H), 3.65 (bs, 2H), 4.25 (bs, 2H). M+=377.1

EXAMPLE 8. SYNTHESIS OF SUL 144 ((2S)-1-(6-HYDROXY-2,5,7,8-TETRAMETHYLCHROMAN-2-CARBONYL)PYRROLIDINE-2-CARBOXYLIC ACID)

(2S)-methyl 1-(6-hydroxy-2,5,7,8-tetramethylchroman-2-carbonyl)pyrrolidine-2-carboxylate (diastereomer 1, 3.5 g, 9.7 mmol) was dissolved in THF/$H_2O$ (60/20 mL). $N_2$ was bubbled through the solution for 1 h. The mixture was cooled in an ice-bath and $LiOH.H_2O$ (1.01 g, 24.2 mmol, 2.5 eq.) was added. The reaction mixture was stirred under $N_2$ at RT overnight. Dowex-50WX8-200 (washed 4× with MeOH/$H_2O$ 3:1) was added as a slurry in MeOH/$H_2O$ (3:1) until the pH=6. The mixture was filtered, washed with MeOH/$HO_2$ (3:1) and concentrated in vacuo. Demi $H_2O$ (50 mL) was added to the concentrate and the solution was freeze dried affording SUL-144 (3.4 g, 9.7 mmol, quant, 99.7% pure) as a off-white foam.

1H-NMR ($CDCl_3$): 1.60 (s, 3H), 1.65-2.30 (m, 14H), 2.60 (m, 2H), 2.81 (m, 1H), 3.49 (m, 1H), 4.01 (t, 1H), 4.50 (d, 1H)

M+=348.1

EXAMPLE 9: SUL 109 FOR COLD ISCHEMIC TOLERANCE OF PORCINE HEARTS

This example studies if SUL 109 as additive to standard heart transplantation protocols will help to prolong the maximal cold ischemic protection of porcine hearts. For long term arrest, for example in case of transplantation, a commonly used solution is CUSTODIOL®. With CUSTODIOL® solution it is possible to keep a heart in a cold ischemic state for up to six hours before reperfusion with warm oxygenated blood is necessary.

Material and Methods

Two hearts were harvested from slaughterhouse pigs and treated as follows. Pigs were stunned by electrical shock to the head and exsanguinated by severing the superior caval vein. After exsanguinations the sternum was quickly opened and the heart and lungs were removed as a whole. The heart was immediately submersed in an ice cold bath and the aorta was cut proximal to the brachocephalic side branches. A 19 mm cannula was inserted in the aorta and tied off. The carefully de-aired cannulla was used to retrogradely administer cold cardioplegic solution. In the first heart, 2 liters of standard CUSTODIOL® with 5000 IU/l of heparin added was administered. The second heart was administered 2 liters of CUSTODIOL® with 5000 IU/l of heparin and 10 ml/l of SUL 109 in 0.9% NaCl at 75 µM. Both hearts were stored in plastic bags filled with the same solutions and transported to the lab on ice at approximately 4° C. Before preparation the hearts were stored at 4° C. for 24 hours. The next day both hearts were prepared to be mounted in the PhysioHeart platform as described in DeHart et al 2011. After de-airing the hearts, retrograde reperfusion of the aorta was started with warm oxygenated blood at 38° C. Both flow of blood and pressure at the aortic root were registered during the experiment.

Results and Findings

First the non SUL109 treated heart was reperfused with blood. This heart showed high vascular resistance at reperfusion resulting in a total coronary blood flow of 0.5 liters per minute at a set aortic pressure of 80 mmHg. Hardly any contractile activity of the heart muscle was visible after 5 minutes, only a slight motion of tissue resembling fibrillation. After some defibrillation by electric shock and assisting the heart with a pacemaker, a vague contraction of the lateral and anterior left ventricle was visible.

The second heart, which was treated with SUL109, was also reperfused with blood. Immediately after the start of reperfusion, the first remarkable difference with the non treated heart occurred. The muscle tissue of the treated heart initially was hard and stiff as the non treated heart but at reperfusion and warming up the heart gradually became less hard and stiff and almost feeling like a normal heart at reperfusion within 6 hours. This resulted in a lower vascular resistance, as observed by a coronary flow of 1 lpm at a perfusion pressure of 80 mmHg. The treated heart immediately displayed more contractile activity compared to the non treated one and after some defibrillation shocks a weak contractive unpaced pattern was observed.

Discussion

In the normal harvesting procedure of the PhysioHeart experiments, the hearts are arrested on a cold cardioplegic solution and transported to the LifeTec Group laboratories for further preparation and surgical interventions. Preparations can take up to 4 hours after which the heart is reactivated by reperfusion with warm oxygenated blood. In order to increase the preparational time, or to allow longer travel time before reperfusion, it would be very useful to be able to protect myocardial tissues during the cold ischemic time. This example shows a clear difference observed between the SUL109 treated heart and the non-treated heart, as the former showed an improved regular contractile activity of the myocardial tissue. Accordingly, using SUL 109 as an additive to standard heart transplantation protocols prolongs the cold ischemic protection.

The invention claimed is:

1. A method for protection of cells comprising adding a compound to a cell, wherein the compound has the structural formula of (I)

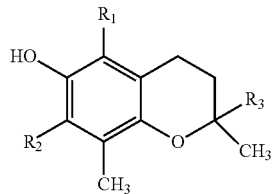

wherein, $R_1$ and $R_2$ are independently selected from the group consisting of $C_1$-$C_6$ alkyl;

$R_3$ is

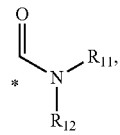

where * indicates the point of attachment of $R_3$ to the remainder of the molecule;

$R_{11}$ and $R_{12}$ are independently selected from alkyl or substituted alkyl groups, or form together with the N atom to which they are attached a saturated or unsaturated 3-8 membered ring, having one or more heteroatoms selected from the group consisting of N, O, or S, wherein the heteroatom is substituted with an alkyl or alkyl alcohol.

2. The method according to claim 1, wherein the protection of cells occurs during storage.

3. The method according to claim 2, wherein the storage occurs at a temperature below 37° C., at about 4° C., at about −20° C. or at about −80° C.

4. The method according to claim 1, where the addition of the compound occurs prior to cooling the cells.

5. The method according to claim 1, wherein the cells are mammalian cultured cells, mammalian primary cells or blood platelets.

* * * * *